(12) United States Patent
Baumgarten et al.

(10) Patent No.: US 8,497,075 B2
(45) Date of Patent: Jul. 30, 2013

(54) METHODS OF IDENTIFYING A MODULATOR THAT INHIBITS THE BINDING BETWEEN EPSTEIN-BARR VIRUS INDUCED RECEPTOR 2 AND CHOLESTEROL DERIVED LIGANDS

(75) Inventors: Birgit Baumgarten, Riehen (CH); Francois Gessier, Altkirch (FR); Andreas Katopodis, Bottinmingen (CH); Richard Knochenmuss, Birmensdorf (CH); Rocco Falchetto, Biubiasco (CH); Silvio Roggo, Nuttenz (CH); Andreas Sailer, Schopfham (DE); Klaus Seuwen, Michelbach-le-Bas (FR); Carsten Spanka, Loerrach (DE); Juan Zhang, Zurich (CH); Sebastien Hannedouche, Namue (BG); Sophie Noel, Welcourt (BG); Marie-Odile Roy, Brussels (BG); Yu Chen, La Jolla, CA (US); Charles Y. Cho, San Diego, CA (US); Wei Li, San Diego, CA (US); Weijun Shen, San Diego, CA (US)

(73) Assignees: Novartis AG, Basel (CH); IRM LLC, Hamilton (BM); Euroscreen SA, Gosselies (BE); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/133,464

(22) PCT Filed: Jul. 12, 2009

(86) PCT No.: PCT/EP2009/066550
§ 371 (c)(1),
(2), (4) Date: Jun. 8, 2011

(87) PCT Pub. No.: WO2010/066689
PCT Pub. Date: Jun. 17, 2010

(65) Prior Publication Data
US 2011/0243923 A1 Oct. 6, 2011

Related U.S. Application Data

(60) Provisional application No. 61/201,326, filed on Dec. 9, 2008.

(51) Int. Cl.
*G01N 33/53* (2006.01)
*C07K 14/435* (2006.01)

(52) U.S. Cl.
USPC .......................................... 435/7.1; 530/350

(58) Field of Classification Search
None
See application file for complete search history.

(56) References Cited

FOREIGN PATENT DOCUMENTS
EP 1286165 A2 2/2003

OTHER PUBLICATIONS

Costagliola S. et al., "Genetic Immunization against the human thyrotropin receptor causes thryroiditis and allows productionof monoclonal antibodies recognizing the native receptor," J Immunol 160(3):1458-1465 (Feb. 1, 1998).
Santa Cruz Biotechnology: "Product Specification Catalog sc-66439 (anti-EB12 antibody)" [Online] 2007, XP002582988 Retreived from the Internet: URL:http://datasheets.scbt.com/sc-66439.pdf> [retrieved on May 20, 2010].
Santa Cruz Biotechnology: "Product Specification Catalog sc-62253 (EB12 siRNA)" [Online] 2007, XP002586876 Retreived from the Internet: URL:http://datasheets.scbt.com/sc-62253.pdf> [retrieved on May 20, 2010].

*Primary Examiner* — Ruixiang Li
(74) *Attorney, Agent, or Firm* — Paul Paglierani

(57) ABSTRACT

The present invention relates to modulators of the interaction between Epstein-Barr Virus induced receptor-2 (EBi2) and cholest-5-ene-3b,7b,25-triol (7,25-dihydroxycholesterol) ("7,25DHC") and/or cholest-5-ene-3b, 7b-diol (7-hydroxycholesterol) ("7HC"). The modulator maybe a small chemical molecule, antibody or other therapeutic protein. Methods of medical treatment and methods of identifying modulators are also described.

8 Claims, 30 Drawing Sheets

Figure 1:
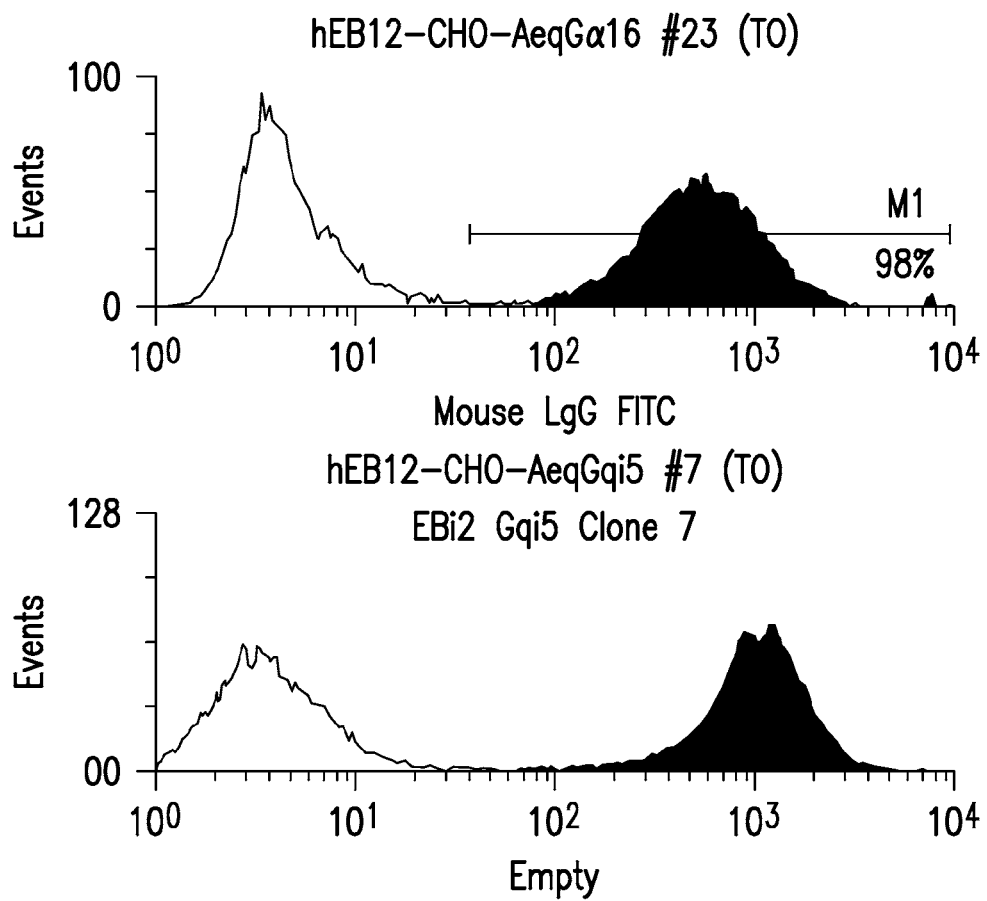

1 = CHO Gqi5
2 = EBi2 or CTRL siRNA
3 = control
4 = CHO Gqi5 EBi2 clone #7

Positive ion mode:

Negative ion mode:

A

LC-MS/MS of 7,25DHC stereoisomers (Reference compounds)

B

A

B

A

B

METHODS OF IDENTIFYING A MODULATOR THAT INHIBITS THE BINDING BETWEEN EPSTEIN-BARR VIRUS INDUCED RECEPTOR 2 AND CHOLESTEROL DERIVED LIGANDS

This application is a U.S. National Phase filing of International Serial No. PCT/EP09/066,550 filed Dec. 7, 2009, and claims priority to U.S. Provisional Application Ser. No. 61/201,326, filed Dec. 9, 2008, the contents of which are incorporated herein by reference in their entirety.

1. FIELD OF THE INVENTION

The present invention relates to modulators, particularly inhibitors of the interaction between cholest-5-ene-3b,7a,25-triol (7a, 25-dihydroxycholesterol) ("7a,25DHC") and/or cholest-5-ene-3b,7a,27-triol (7a, 27-dihydroxycholesterol) ("7a,27DHC") and/or cholest-5-ene-3b,7b,25-triol (7b, 25-dihydroxycholesterol) ("7b,25DHC") and/or cholest-5-ene-3b,7b,27-triol (7b, 27-dihydroxycholesterol) ("7b, 27DHC") and/or cholest-5-ene-3b,7a-diol (7a-hydroxycholesterol) ("7aHC") and/or cholest-5-ene-3b,7b-diol (7b-hydroxycholesterol) ("7bHC"), 25-diol (25-hydroxycholesterol) ("25HC") and Epstein-Barr Virus induced receptor 2 ("EBI2"). More particularly the present invention relates to pharmaceutical compositions comprising said modulators and methods of treating diseases or disorders responsive to modulating said interaction. Other aspects, objects and advantages of the present invention will be apparent from the description below.

2. BACKGROUND OF THE INVENTION

The Epstein-Barr virus (EBV) induced gene 2 EBI2, also called GPR183, codifies for a receptor which belongs to the superfamily of Rhodopsin-like 7™ receptors (seven transmembrane segment receptors), also known as G-protein coupled receptors (GPCRs). EBI2, is an orphan G-protein coupled receptor for which no ligand is known. EBI2 was cloned in 1993 as one of the most up-regulated genes (>200 fold) in Epstein-Barr virus (EBV)-infected Burkitt lymphoma cells (Birkenbach, M., et al. (1993). Epstein-Barr virus-induced genes: first lymphocyte-specific G protein-coupled peptide receptors. J. Virol. 67, 2209-2220.). The EBI2 gene is localized on chromosome 13q32.3. EBI2 shares approximately 35% homology at the amino acid level with the fowlpox virus FPV206, 30-32% with P2Y5 and P2Y9 receptors. EBI2 is also closely related to the orphan 7™ receptor GPR18 and the two lipid receptors cysteinyl leukotriene receptor 1 and -2 (CysLT1, and -2) (25% and 28% homology respectively).

Real-time PCR of EBV-infected cells showed high expression of EBI2 during latent as well as lytic viral replication (Rosenkilde, et al. (2006) Molecular pharmacological phenotyping of EBI2—An orphan seven-transmembrane receptor with constitutive activity. Journal of Biological Chemistry 281 [19], 13199-13208.). Very high expression of the EBI2 gene was reported in peripheral blood mononuclear cells (PBMCs), in lymphoid tissue (spleen and lymph node) and lung tissue (Birkenbach, M., et al. (1993); Rosenkilde, M. M. et al. (2006)). EBI2 expression was shown to be highest in B-lymphocytes, followed by T lymphocytes, NK-cells and lowest in monocytes (Rosenkilde, M. M. et al. (2006), Cahir-McFarland, E. D. et al. (2004). Role of NF-kappa B in cell survival and transcription of latent membrane protein 1-expressing or Epstein-Barr virus latency III-infected cells. J. Virol. 78, 4108-4119.). The expression profile of EBI2 suggests a role in immune system modulation. Finally, constitutive signaling through Gαi and cell surface localization of EBI2 was also demonstrated (Rosenkilde, M. M. et al. (2006)).

It is an object of the present invention to identify ligands for EBI2.

3. SUMMARY OF THE INVENTION

The present invention is based, at least in part, on finding that 7,25DHC and 7,27DHC and 7HC and 25HC are ligands for EBI2.

In accordance with a first aspect of the present invention there is provided a modulator (e.g. inhibitor) of the interaction between 7,25DHC and/or 7,27DHC and/or 7HC and/or 25HC (i.e. ligand) and EBI2 (e.g. human EBI2), preferably between 7a,25DHC and/or 7b,25DHC and/or 7a,27DHC and/or 7b,27DHC and/or 7aHC and/or 7bHC and/or 25HC and EBI2 (e.g. human EBI2), especially 7a,25DHC and EBI2 (e.g. human EBI2).

In other embodiments of this aspect, the modulator binds with 7,25DHC and/or 7,27DHC and/or 7HC and/or 25HC and/or EBI2, preferably with 7a,25DHC and/or 7b,25DHC and/or 7a,27DHC and/or 7b,27DHC and/or 7aHC and/or 7bHC and/or 25HC and/or EBI2, more preferably with 7a,25DHC and/or EBI2, and inhibits the interaction between ligand and EBI2. The inhibitor may be a therapeutic protein, such as an antibody or antibody fragment, or a small molecule chemical entity.

In other embodiments of this aspect, the modulator modulates (e.g. inhibits) the endogenous production of 7,25DHC and/or 7,27DHC and/or 7HC and/or 25HC production, preferably the modulator modulates (e.g. inhibits) the endogenous production of 7a,25DHC and/or 7b,25DHC and/or 7a,27DHC and/or 7b,27DHC and/or 7aHC and/or 7bHC and/or 25HC, by for example, inhibiting the endogenous enzymatically mediated production of 7,25DHC and/or 7,27DHC and/or 7HC and/or 25HC production, preferably the modulator inhibits the endogenous enzymatically mediated production of 7a,25DHC and/or 7b,25DHC and/or 7a,27DHC and/or 7b,27DHC and/or 7aHC and/or 7bHC and/or 25HC. The modulator may inhibit the enzyme responsible for the conversion of the immediate precursor of 7,25DHC and/or 7,27DHC and/or 7HC and/or 25HC, preferably of precursors of the immediate precursor of 7a,25DHC and/or 7b,25DHC to 7a,25DHC and/or 7b,25DHC, respectively.

In some other embodiments of this aspect the modulator is selected from the group consisting of; small chemical entity, antibody, Adnectin, Ankyrin, Maxybody/Avimer, Affibody, anticalin, Affilin, anti-sense oligonucleotide, short-interfering RNA (siRNA). The modulator may be an antibody or antibody fragment. When the modulator is an antibody, it may comprise human constant region and/or may have an IgG isotype (e.g. IgG1 or IgG4) and/or may be a chimeric, human or humanised antibody.

When the modulator is an antibody fragment, the antibody fragment is selected from the group consisting of; Fab, Fab', F(ab')2, Fv, ScFv, VH domain, VHH domain.

In further other embodiments of this aspect the modulator is an inhibitor of EBI2 expression. Such inhibitors maybe an anti-sense oligonucleotide comprising or consisting essentially of a sequence (a) capable of forming a stable triplex with a portion of the EBI2 gene, or (b) capable of forming a stable duplex with a portion of an mRNA transcript of the EBI2 gene under physiological conditions. Alternatively, or in addition, the inhibitor may be an antisense oligonucleotide or a short-interfering RNA (siRNA) molecule which inhibits the expression of EBI2 protein (e.g. is capable of interfering with the translation of the EBI2 transcript).

In a second aspect of the invention there is provided a pharmaceutical composition comprising a modulator of the first aspect supra together with a pharmaceutically acceptable carrier or diluent.

In some embodiments of this second aspect, the pharmaceutical composition may comprise instructions for use.

In a third aspect of the invention there is provided a method of treating a mammalian patient, particularly a human patient afflicted with a disease or disorder responsive to modulation of the interaction between 7,25DHC and/or 7,27DHC and/or 7HC and/or 25HC and EBI2, preferably between 7a,25DHC and/or 7b,25DHC and/or 7a,27DHC and/or 7b,27DHC and/or 7aHC and/or 7bHC and/or 25HC and EBI2, which method comprises administering a therapeutically effective amount of the pharmaceutical aspect of the second aspect supra.

In a fourth aspect of the invention there is provided a prophylactic method of treating a mammalian patient, particularly a human patient afflicted with a disease or disorder responsive to modulation of the interaction between 7,25DHC and/or 7,27DHC and/or 7HC and/or 25HC and EBI2, preferably between 7a,25DHC and/or 7b,25DHC and/or 7a,27DHC and/or 7b,27DHC and/or 7aHC and/or 7bHC and/or 25HC and EBI2, which method comprises administering a therapeutically effective amount of the pharmaceutical aspect of the second aspect supra.

In some embodiments of the these third and fourth aspects, the disease or disorders is selected from the group consisting of; hypertension, angina pectoris, atherosclerosis, congestive heart failure, stroke, obesity, metabolic syndrome, autoimmune diseases such as arthritis, (especially rheumatoid arthritis) and lupus, atopic conditions such as asthma and atopic dermatitisasthma, COPD, pulmonary hypertension, viral infections such as EBV, HIV, hepatitis (A or C), fatty liver disease, liver cirrhosis (particularly alcohol induced liver cirrhosis), cancer, dyslipidemia, diabetes (particularly type II), transplant rejection, irritable bowel syndrome, inflammatory bowel disease, diseases of chronic inflammation, allergy, psoriasis, cystic fibrosis, hypercholesterolaemia, renal disease multiple sclerosis.

In a fifth aspect there is provided a process for the manufacture of a modulator of the first and a pharmaceutical composition of the second aspect supra.

In a sixth aspect of the invention, there is provided a method of identifying a modulator, particularly an inhibitor of the interaction between 7,25DHC and/or 7HC and/or 25HC and EBI2, preferably between 7a,25DHC and/or 7,27DHC and/or 7b,25DHC and/or 7a,27DHC and/or 7b,27DHC and/or 7aHC and/or 7bHC and/or 25HC and EBI2 which method comprises contacting 7,25DHC and/or 7HC and/or EBI2, preferably between 7a,25DHC and/or 7b,25DHC and/or 7a,27DHC and/or 7b,27DHC and/or 7aHC and/or 7bHC and/or 25HC and EBI2, with a candidate modulator and observing a modulation of the interaction between ligand and receptor.

4. DETAILED DESCRIPTION OF THE INVENTION

Throughout this specification, the term "7,25DHC", "7,27DHC", "25HC" and "7HC" includes all enantiomers, stereoisomers, racemate mixtures and optically pure isomer forms thereof. Thus throughout this specification, embodiments of the invention mentioning "7,25DHC" and/or "7,27DHC" and/or "7HC" and/or "25HC" should be construed as referring to individual embodiments of a racemate mixture of the indicated ligand as well as to individual embodiments of optically pure isomer forms of the indicated ligand. The terms "7a,25DHC" and "7a,27DHC" throughout this specification indicates only optically pure or substantially optically pure isomer forms. Thus, the terms "7a,25DHC" and "7a,27DHC" should be construed as referring to individual embodiments of optically pure isomer forms of the indicated ligands. Similarly, the terms "7b,25DHC", "7b,27DHC", "7aHC", "7bHC" and "25HC" should also be construed as referring to individual embodiments of optically pure isomer forms of the indicated ligands. Therapeutic proteins, polynucleotides and oligonucleotides as described herein are in isolated form. Reference in section 4 of this specification to "EBI2" refers to human EBI2 unless otherwise specified. Likewise, reference to diseases or disorders refers to human diseases or disorders.

4.1—Therapeutic Proteins

A therapeutic protein of the present invention maybe an antibody, Adnectin, Ankyrin, Maxybody/Avimer, Affibody, anticalin, or Affilin.

4.1.1.—Antibodies

Antibodies of the present invention maybe in any of a number of formats well known to the skilled person. These formats include intact antibodies, various antibody fragments and other engineered formats as described below. In preferred forms, antibodies of the present invention are provided as a monoclonal population.

4.1.1.1—Intact Antibodies

Intact antibodies include heteromultimeric glycoproteins comprising at least two heavy and two light chains. Aside from IgM, intact antibodies are usually heterotetrameric glycoproteins of approximately 150 KDa, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain (VH) followed by a number of constant regions. Each light chain has a variable domain (VL) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two type called Kappa or Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called Framework regions (FR). The variable domains of intact heavy and light chains each comprise four FR connected by three CDRs. The CDRs in each chain are held together in close proximity by the FR regions and with the CDRs from other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγr receptor, half-life/ clearance rate via neonatal Fc receptor (FcRn) and complement dependent cytoxicity via the C1q component of the complement cascade.

Thus in one embodiment of the invention there is provided an intact therapeutic antibody of binding 7,25DHC and/or 7,27DHC and/or 7HC and/or 25HC and/or EBI2 and inhibiting the interaction between 7,25DHC and/or 7,27DHC and/or 7HC and/or 25HC and EBI2. In preferred embodiments of the invention, the intact therapeutic antibody binds 7a,25DHC and/or 7b,25DHC and/or 7a,27DHC and/or 7b,27DHC and/or 7aHC and/or 7bHC and/or 25HC and/or EBI2 and inhibits the interaction between 7a,25DHC and/or 7b,25DHC and/or 7a,27DHC and/or 7b,27DHC and/or 7aHC and/or 7bHC and/or 25HC and EBI2. Such antibodies typically have a human constant region of an IgG isotype such as IgG1 or IgG4 and maybe human, humanized or chimeric.

4.1.1.1.1 Human Antibodies

Human antibodies may be produced by a number of methods known to those of skill in the art. Human antibodies can be made by the hybridoma method using human myeloma or mouse-human heteromyeloma cells lines see Kozbor J. Immunol. 133, 3001, (1984) and Brodeur, Monoclonal Antibody Production Techniques and Applications, pp 51-63 (Marcel Dekker Inc, 1987). Alternative methods include the use of phage libraries or transgenic mice both of which utilize human V region repertoires (see Winter G, (1994), Annu. Rev. Immunol. 12, 433-455, Green L L (1999), J. Immunol. Methods 231, 11-23).

Several strains of transgenic mice are now available wherein their mouse immunoglobulin loci has been replaced with human immunoglobulin gene segments (see Tomizuka K, (2000) PNAS 97, 722-727; Fishwild D M (1996) Nature Biotechnol. 14, 845-851. Mendez M J, 1997, Nature Genetics, 15, 146-156). Upon antigen challenge such mice are capable of producing a repertoire of human antibodies from which antibodies of interest can be selected. Of particular note is the Trimera™ system (see Eren R et al, (1988) Immunology 93:154-161) where human lymphocytes are transplanted into irradiated mice, the Selected Lymphocyte Antibody System (SLAM, see Babcook et al, PNAS (1996) 93: 7843-7848) where human (or other species) lymphocytes are effectively put through a massive pooled in vitro antibody generation procedure followed by deconvulated, limiting dilution and selection procedure and the Xenomouse™ (Abgenix Inc). An alternative approach is available from Morphotek Inc using the Morphodoma™ technology.

Phage display technology can be used to produce human antibodies (and fragments thereof), see McCafferty; Nature, 348, 552-553 (1990) and Griffiths A D et at (1994) EMBO 13: 3245-3260. According to this technique antibody V domain genes are cloned in frame into either a major or minor coat of protein gene of a filamentous bacteriophage such as M13 or fd and displayed (usually with the aid of a helper phage) as function antibody fragments on the surface of the phage particle. Selections based on the function properties of the antibody result in selection of the gene encoding the antibody exhibiting these properties. The phage display technique can be used to select antigen specific antibodies from libraries made from human B cells taken from individuals afflicted with a disease or disorder described above or alternatively from unimmunized human donors (see Marks; J Mol Bio 222, 581-591, 1991). Where an intact human antibody is desired comprising an Fc domain it is necessary redone the phage displayed derived fragment into a mammalian expression vectors comprising the desired constant regions and establishing stable expressing cell lines.

The technique of affinity maturation (Marks; Bio/technol 10, 779-783 (1992)) may be used to provide binding affinity wherein the affinity of the primary human antibody is improved by sequentially replacing the H and L chain V regions with naturally occurring variants and selecting on the basis of improved binding affinities. Variants of this technique such as 'epitope imprinting' are now also available, see WO 93/06213. See also Waterhouse; Nucl Acids Res 21, 2265-2266 (1993).

Thus in one embodiment of the invention there is provided an intact therapeutic (human) antibody capable of binding 7,25DHC and/or 7,27DHC and/or 7HC and/or 25HC and/or EBI2 and inhibiting the interaction between 7,25DHC and/or 7,27DHC and/or 7HC and/or 25HC and EBI2. In preferred embodiments of the invention, the intact therapeutic human antibody binds 7a,25DHC and/or 7b,25DHC and/or 7a,27DHC and/or 7b,27DHC and/or 7aHC and/or 7bHC and/or 25HC and/or EBI2 and inhibits the interaction between 7a,25DHC and/or 7b,25DHC and/or 7a,27DHC and/or 7b,27DHC and/or 7aHC and/or 7bHC and/or 25HC and EBI2. In typical embodiments the intact therapeutic human antibody comprises a constant region of an IgG isotype, e.g. IgG1 or IgG4.

4.1.1.1.2 Chimaeric and Humanised Antibodies

The use of intact non-human antibodies in the treatment of human diseases or disorders carries with it the potential for the now well established problems of immunogenicity, that is the immune system of the patient may recognises the non-human intact antibody as non-self and mount a neutralising response. This is particularly evident upon multiple administration of the non-human antibody to a human patient. Various techniques have been developed over the years to overcome these problems and generally involve reducing the composition of non-human amino acid sequences in the intact antibody whilst retaining the relative ease in obtaining non-human antibodies from an immunised animal, e.g. mouse, rat or rabbit. Broadly two approaches have been used to achieve this. The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimaeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody of the invention, e.g. DNA encoding SEQ ID NO 1, 2, 3, 4, 5 and 6 described supra). Hybridoma cells serve as a typical source of such DNA. Once isolated, the DNA is placed into expression vectors which are then transfected into host cells such as *E. Coli*, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework region. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ('donor' antibodies) onto human framework ('acceptor framework') and constant regions (see Jones et al (1986) Nature 321, 522-525 and Verhoeyen M et al (1988) Science 239, 1534-1536). However, CDR grafting per se may not result in the complete retention of antigen-binding properties and it is frequency found that some framework residues (sometimes referred to as 'backmutations') of the donor antibody need to be preserved in the humanised compound If significant antigen-binding affinity is to be recovered (see Queen C et al (1989) PNAS 86, 10, 029-10,033, Co, M et al (1991) Nature 351, 501-502). In this case, human V regions showing the greatest sequence homology to the non-human donor antibody are chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody may be used to help identify such structurally important residues, see WO99/48523.

Alternatively, humanisation may be achieved by a process of 'veneering'. A statistical analysis of unique human and murine immunoglobulin heavy and light chain variable regions revealed that the precise patterns of exposed residues are different in human and murine antibodies, and most individual surface positions have a strong preference for a small number of different residues (see Padlan E A, et al; (1991) Mol Immunol 28, 489-498 and Pedersen J T et al (1994) J Mol Biol 235; 959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region 'invisible' to the human immune system (see also Mark G E et al (1994) in Handbook of Experimental Pharmacology vol 113: The pharmacology of monoclonal Antibodies, Springer-Verlag, pp 105-134). This procedure of humanisation is referred to as 'veneering' because only the surface of the antibody is altered, the supporting residues remain undisturbed.

Thus in one embodiment of the invention there is provided an intact therapeutic humanised antibody capable of binding 7,25DHC and/or 7,27DHC and/or 7HC and/or 25HC and/or EBI2 and inhibiting the interaction between 7,25DHC and/or 7,27DHC and/or 7HC and/or 25HC and EBI2. In preferred embodiments of the invention, the intact therapeutic humanised antibody binds 7a,25DHC and/or 7b,25DHC and/or 7a,27DHC and/or 7b,27DHC and/or 7aHC and/or 7bHC and/or 25HC and/or EBI2 and inhibits the interaction between 7a,25DHC and/or 7b,25DHC and/or 7a,27DHC and/or 7b,27DHC and/or 7aHC and/or 7bHC and/or 25HC and EBI2. In typical embodiments the intact therapeutic human antibody comprises a constant region of an IgG isotype, e.g. IgG1 or IgG4.

4.1.1.1.3 Bispecific Antibodies

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities, (see Millstein et al, Nature 305, 537-539 (1983), WO93/08829 and Traunecker et al, EMBO, 10, 1991, 3655-3659). Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions and, if desired, the L chain are inserted into separate expression vectors and are the contransfected into a suitable host organism. It is possible though to insert the coding sequences for two or all three chains into one expression vector. In one preferred approach, the bispecific antibody is composed of an H chain with a first binding specificity in one arm and an H-L chain pair, providing a second binding specificity in the other arm, see WO94/04690. Also see Suresh et al, Methods in Enzymology 121, 210, 1986.

In one embodiment of the invention there is provided a bispecific therapeutic antibody wherein at least one binding specificity of said antibody is for 7,25DHC or 7,27DHC or 7HC or 25HC and the second specificity is for EBI2. In preferred embodiments of the invention, the bispecific therapeutic antibody has at least one binding specificity for 7a,25DHC and/or 7b,25DHC and/or 7a,27DHC and/or 7b,27DHC and/or 7aHC and/or 7bHC and/or 25HC and the second specificity for EBI2 and inhibits the interaction between 7a,25DHC and/or 7b,25DHC and/or 7a,27DHC and/or 7b,27DHC and/or 7aHC and/or 7bHC and/or 25HC and EBI2. In preferred forms the bispecific antibody comprises a primate, e.g. human antibody of a IgG (e.g. IgG1 or IgG4) isotype.

4.1.1.1.4 Antibody Fragments

In certain embodiments of the invention there is provided therapeutic antibody fragments which modulate (e.g. inhibit) the interaction between 7,25DHC and/or 7,27DHC and/or 7HC and EBI2. Such fragments may be functional antigen binding fragments of intact and/or humanised chimaeric antibodies such as Fab, Fab', $F(ab_1)_2$, Fv, ScFv fragments of the antibodies described supra.

Traditionally, such fragments are produced by the proteolytic digestion of intact antibodies by e.g. papain digestion (see for example WO 94/29348) but may be produced directly from recombinantly transformed host cells. For the production of ScFv, see Bird et al; (1988) Science, 242, 423-426. In addition, antibody fragments may be produced using a variety of engineering techniques as described below. FV fragments appear to have lower interaction energy of their two chains than Fab fragments. To stabilise the association of the VH and VL domains, they have been linked with peptides (Bird et al, (1988) Science, 242, 423-426, Huston et al, PNAS, 85, 5879-5883), disulphide bridges (Glockshuber et al, (1990) Biochemistry, 29, 1362-1367) and 'knob in hole' mutations (Zhu et al (1997), Protein Sci., 6, 781-788). ScFv fragments can be produced by methods well known to those skilled in the art (see Whitlow et al (1991), Methods companion Methods Enzymol, 2, 97-105 and Huston et al (1993) Int Rev Immunol 10, 195-217. ScFv may be produced in bacterial cells such as E. Coli but are more preferably produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFv containing an additional C terminal cysteine by chemical coupling (Adams et al (1993) Can Res 53, 4026-4034 and McCartney et al (1995) Protein Eng, 8, 301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to 3 and 12 residues to form 'diabodies' (see Holliger et al PNAS (1993), 90, 6444-6448). Reducing the linker still further can result in ScFV trimers ('triabodies', see Kortt et al (1997) Protein Eng, 10, 423-433) and tetramers ('tetrabodies', see Le Gall et al (1999) FEBS Lett, 453, 164-168). Construction of bialent ScFV compounds can also be achieved by genetic fusion with protein dimerzing motifs to form 'miniantibodies' (see Pack et al (1992) Biochemistry 31, 1579-1584) and 'minibodies' (see Hu et al (1996), Cancer Res. 56, 3055-3061). ScFv-Sc-Fv tandems ((ScFV)$_2$) may also be produced by linking two ScFV units by a third peptide linger, (see Kurucz et al (1995) J Immunol, 154, 4576-4582). Bispecific diabodies can be produced through the noncovalent association of two single chain fusion products consisting of VH domain from one antibody connected by a short linker to the VL domain of another antibody, (see Kipriyanov et al (1998), Int J Can 77, 763-772). The stability of such bispecific diabodies can be enhanced by the introduction of disulphide bridges or 'knob in hole' mutations as described supra or by the formation of single chain diabodies (ScDb) wherein two hydrid ScFv fragments are connected through a peptide linker (see Kontermann et al (1999) J Immunol Methods 226, 179-188). Tetravalent bispecific compounds are available by e.g fusing a ScFv fragment to the CH3 domain of an IgG compound or to a Fab fragment through the hinge region (see Coloma et al (1997) Nature Biotechnol, 15, 159-163). Alternatively, tetravalent bispecific compounds have been created by the fusion of bispecific single chain diabodies (see Alt et al (1999) FEBS Lett 454, 90-94). Smaller tetravalent bispecific compounds can also be formed by the dimerization of either ScFv-ScFv tandems with a linker containing a helix-loop-helix motif (DiBi miniantibodies, see Muller et al (1998) FEBS Lett 432, 45-49) or a single chain compound comprising four antibody variable domains (VH and VL) in an orientation preventing intramolecular pairing (tandem diabody, see Kipriyanov et al, (1999) J Mol Biol 293, 41-56). Bispecific F9ab')$_2$ fragments can be created by chemical coupling of Fab' fragments or by heterodimerization through leucine zippers (see Shalaby et al (1992) J Exp Med 175, 217-225 and Kostelny et al (1992), J Immunol 148 1547-1553). Also available are isolated VH and VL domains (Domantis plc), see U.S. Pat. No. 6,248,516; U.S. Pat. No. 6,291,158; U.S. Pat. No. 6,172,197 and isolated VHH domain antibodies (Nanobodies). These domain and nanobodies may be dual specific having one specificity directed to a half life extending protein such as human serum albumin (HSA). Such domain and nanobodies both monospecific for a NRG1 protein of the invention and further dual specific for a half life extending protein such as HSA are specifically contemplated by the invention.

In one embodiment there is provided a therapeutic antibody fragment (e.g. ScFv, Fab, Fab', F(ab')$_2$) or an engineered antibody fragment as described supra that binds with 7,25DHC and/or 7,27DHC and/or 7HC and/or 25HC and/or EBI2 and inhibits the interaction between ligand and receptor. In preferred embodiments of the invention, the therapeutic antibody fragment or the engineered antibody fragment binds 7a,25DHC and/or 7b,25DHC and/or 7a,27DHC and/or 7b,27DHC and/or 7aHC and/or 7bHC and/or 25HC and/or EBI2 and inhibits the interaction between 7a,25DHC and/or 7b,25DHC and/or 7a,27DHC and/or 7b,27DHC and/or 7aHC and/or 7bHC and/or 25HC and EBI2.

4.1.1.1.5 Heteroconivate Antibodies

Heteroconjugate antibodies also form an embodiment of the present invention. Heteroconjugate antibodies are composed of two covalently joined antibodies formed using any convenient cross-linking methods. See, for example, U.S. Pat. No. 4,676,980.

4.1.1.1.6 Other Modifications

The interaction between the Fc region of an antibody and various Fc receptors (FcγR) is believed to mediate the effector functions of the antibody which include antibody-dependent cellular cytotoxicity (ADCC), fixation of complement, phagocytosis, and half-life/clearance of the antibody. Various modifications to the Fc region of antibodies of the invention may be carried out depending on the desired property. For example, specific mutations in the Fc region to render an otherwise lytic antibody, non-lytic is detailed in EP 0629 240B1 and Ep 0307 434B2 or one may incorporate a salvage receptor binding epitope into the antibody to increase serum half-life, see U.S. Pat. No. 5,739,277. There are five currently recognised human Fcγ, FcγR (I), FCγRIIb, FcγRIIIa and neonatal FcRn. Shields et al, (2001) J Biol Chem 276, 6591-6604 demonstrated that a common set of IgG1 residues is involved in binding all FcγRs, while FCγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to DcγRII or FcγRIII with reduction in binding to the other receptor (e.g. Ser298Ala improved binding to FcγRIII and reduced binding to FcγRII). For FcγRIIIa, the best binding IgG1 variants had combined alanine substitutions at Ser-298, Glu-333 and Ls-334. The neonatal FcRn receptor is believed to be involved in both antibody clearance and the transcytosis across tissues (see Junghans R P (1997) Immunol Res 16, 2957 and Ghetie et al (2000) Annu Rev Immunol 18, 739-766). Human IgG1 residues determined to interact directly with human FcRn included Ile253, Ser254, Lys288, Thr307, Gln311, Asn434 and His435. Switches at any of these positions described in this section may enable increased serum half-life and/or altered effector properties of antibodies of the invention and therefore forms an embodiment of the invention.

Other modifications include glycosylation variants of the antibodies of the invention. Glycosylation of antibodies at conserved positions in their constant regions is known to have a profound effect on antibody function, particularly effector functioning such as those described above, see for example, Boyd et al (1996), Mol Immunol 32, 1311-1318. Glycosylation variants of the therapeutic antibodies or antigen binding fragments thereof of the present invention wherein one or more carbohydrate moiety is added, substituted, deleted or modified are contemplated. Introduction of an asparagine-X-serin or asparagine-X-threonine motif creates a potential side for enzymatic attachment of carbohydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactrosyltransferace and/or alpha, 2, 3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al, Science (2004), 303, 371; Sears et al, Science (2001), 291, 2344; Wacker et al (2002), Science 298, 1790; Davis et al (2002), Chem Rev 102, 579; Hang et al (2001), Acc Chem Res 34, 727. Thus the invention contemplates a plurity of therapeutic (monoclonal) antibodies (which may be of the IgG isotype, e.g. IgG1) as herein described comprising a defined number (e.g. 7 or less, for example 5 or less such as two or a single) glycoform(s) or said antibodies or antigen binding fragments thereof.

Further embodiments of the invention include therapeutic antibodies of the invention or antigen binding fragments thereof coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments (see Koumenis I L et al (2000) Int J Pharmaceut 198; 83-95.

4.2 Adnectins—Compound Therapeutics

The adnectin scaffolds are based on fibronectin type III domain (e.g., the tenth module of the fibronectin type III (10 Fn3 domain). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands. (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based compounds can be used as scaffolds where the loop regions of the compound can be replaced with CDRs of the invention using standard cloning techniques. Accordingly, in some embodiments there is provided an adnectin compound that binds with 7,25DHC and/or 7,27DHC and/or 7HC and/or 25HC and/or EBI2 and inhibits the interaction between ligand and receptor. In preferred embodiments, the adnectin compound binds with 7a,25DHC and/or 7b,25DHC and/or 7a,27DHC and/or 7b,27DHC and/or 7aHC and/or 7bHC and/or 25HC and/or EBI2 and inhibits the interaction between ligand and receptor.

4.3 Ankyrin—Molecular Partners

This technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display. Accordingly, in some embodiments there is provided an Ankyrin compound that binds with 7,25DHC and/or 7,27DHC and/or 7HC and/or 25HC and/or EBI2 and inhibits the interaction between ligand and receptor. In preferred embodiments, the adnectin compound binds with 7a,25DHC and/or 7b,25DHC and/or 7a,27DHC and/or 7b,27DHC and/or 7aHC and/or 7bHC and/or 25HC and/or EBI2 and inhibits the interaction between ligand and receptor.

4.4 Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, US20040175756; US20050053973; US20050048512; and US20060008844. Accordingly, in some embodiments there is provided an Maxybody compound that binds with 7,25DHC and/or 7,27DHC and/or 7HC and/or 25HC and/or EBI2 and inhibits the interaction between ligand and receptor. In preferred embodiments, the Maxybody compound binds with 7a,25DHC and/or 7b,25DHC and/or 7a,27DHC and/or 7b,27DHC and/or 7aHC and/or 7bHC and/or 25HC and/or EBI2 and inhibits the interaction between ligand and receptor.

4.5 Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® compounds mimic antibodies, they have a molecular weight of 6 kDa, compared to the molecular weight of antibodies, which is 150 kDa. In spite of its small size, the binding site of Affibody® compounds is similar to that of an antibody. Accordingly, in some embodiments there is provided an Protein A-affibody compound that binds with 7,25DHC and/or 7,27DHC and/or 7HC and/or 25HC and/or EBI2 and inhibits the interaction between ligand and receptor. In preferred embodiments, the Protein A-affibody compound binds with 7a,25DHC and/or 7b,25DHC and/or 7a,27DHC and/or 7b,27DHC and/or 7aHC and/or 7bHC and/or 25HC and/or EBI2 and inhibits the interaction between ligand and receptor.

4.6 Anticalins—*Pieris*

Anticalins® are products developed by the company *Pieris ProteoLab AG*. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target compounds of different shape with high affinity and specificity.

One protein of lipocalin family, the bilin-binding protein (BBP) of *Pieris Brassicae* has been used to develop anticalins by mutagenizing the set of four loops. One example of a patent application describing "anticalins" is PCT WO 199916873.

Accordingly, in some embodiments there is provided an anticalin compound that binds with 7,25DHC and/or 7,27DHC and/or 7HC and/or 25HC and/or EBI2 and inhibits the interaction between ligand and receptor. In preferred embodiments, the anticalin compound binds with 7a,25DHC and/or 7b,25DHC and/or 7a,27DHC and/or 7b,27DHC and/or 7aHC and/or 7bHC and/or 25HC and/or EBI2 and inhibits the interaction between ligand and receptor.

4.7 Affilin—Scil Proteins

Affilin™ compounds are small non-immunoglobulin proteins which are designed for specific affinities towards proteins and small compounds. New Affilin™ compounds can be very quickly selected from two libraries, each of which is based on a different human derived scaffold protein. Affilin™ compounds do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368. Accordingly, in some embodiments there is provided an Affilin compound that binds with 7,25DHC and/or 7,27DHC and/or 7HC and/or 25HC and/or EBI2 and inhibits the interaction between ligand and receptor. In preferred embodiments, the Affilin compound compound binds with 7a,25DHC and/or 7b,25DHC and/or 7a,27DHC and/or 7b,27DHC and/or 7aHC and/or 7bHC and/or 25HC and/or EBI2 and inhibits the interaction between ligand and receptor.

4.7.1 Other Therapeutic Modalities

As noted previously, other therapeutic modalities of the invention include modulators (particularly inhibitors) of EBI2 which exert their effect on their target prior to protein expression. Examples include anti-sense oligonucleotides that comprise (or consist essentially of) a sequence (a) capable of forming a stable triplex with a portion of the EBI2 (particularly NRG1β1) gene, or (b) capable of forming a stable duplex with a portion of an mRNA transcript of the EBI2 gene under physiological conditions. Other examples include molecules that can participate in the phenomena of "RNA interference". RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. Conveniently, the dsRNA can be produced from a single promoter in a recombinant vector or host cell, where the sense and anti-sense sequences are flanked by an unrelated sequence which enables the sense and anti-sense sequences to hybridise to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated.

The DNA therefore comprises both sense and antisense sequences that, when transcribed into RNA, can hybridise to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous mammalian system that destroys both the double stranded RNA and also the homologous RNA transcript from the target mammalian gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilise the molecule. The RNA molecule may be expressed under the control of a RNA polymerase II or RNA polymerase HI promoter. Examples of the latter include tRNA or snRNA promoters.

Preferred small interfering RNA ("siRNA") molecules comprise a nucleotide sequence that is identical to about 19-21 contiguous nucleotides of the target mRNA.

Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the mammal in which it is to be introduced, for example as determined by standard BLAST search.

MicroRNA regulation is a clearly specialised branch of the RNA silencing pathway that evolved towards gene regulation, diverging from conventional RNAi/PTGS.

MicroRNAs are a specific class of small RNAs that are encoded in gene-like elements organised in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al. 2005; Almeida and Allshire, 2005).

4.8 Production Methods

Therapeutic proteins of the invention, and particularly antibodies maybe produced as a polyclonal population but are more preferably produced as a monoclonal population (that is as a substantially homogenous population of identical antibodies directed against a specific antigenic binding site). It will of course be apparent to those skilled in the art that a population implies more than one antibody entity. Antibodies of the present invention may be produced in transgenic organisms such as goats (see Pollock et al (1999), J. Immunol. Methods 231:147-157), chickens (see Morrow K J J (2000) Genet. Eng. News 20:1-55, mice (see Pollock et al) or plants (see Doran P M, (2000) Curr. Opinion Biotechnol. 11, 199-

204, Ma J K-C (1998), Nat. Med. 4; 601-606, Baez J e. al, BioPharm (2000) 13: 50-54, Stoger E et al; (2000) Plant Mol. Biol. 42:583-590). Antibodies may also be produced by chemical synthesis. However, antibodies and other therapeutic proteins of the invention are typically produced using a recombinant cell culturing technology well known to those skilled in the art. A polynucleotide encoding the antibody is isolated and inserted into a replicable vector such as a plasmid for further cloning (amplification) or expression. One useful expression system is a glutamate synthetase system (such as sold by Lonza Biologies), particularly where the host cell is CHO or NSO (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and transfected into the same host cell or, if desired both the heavy chain and light chain can be inserted into the same vector for transfection into the host cell. Thus according to one aspect of the present invention there is provided a process of constructing a vector encoding the light and/or heavy chains of a therapeutic antibody or antigen binding fragment thereof of the invention, which method comprises inserting into a vector, a polynucleotide encoding either a light chain and/or heavy chain of a therapeutic antibody of the invention.

4.8.1 Signal Sequences

Antibodies of the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin Il leaders. For yeast secretion the signal sequences may be a yeast invertase leader, [alpha] factor leader or acid phosphatase leaders see e.g. WO90/13646. In mammalian cell systems, viral secretory leaders such as herpes simplex gD signal and a native immunoglobulin signal sequence are available. Typically the signal sequence is ligated in reading frame to DNA encoding the antibody of the invention.

4.8.2 Origin of Replication

Origin of replications are well known in the art with pBR322 suitable for most gram-negative bacteria, 2μ plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

4.8.3 Selection Marker

Typical selection genes encode proteins that (a) confer resistance to antibiotics or other toxins e.g. ampicillin, neomycin, methotrexate or tetracycline or (b) complement auxotrophic deficiencies or supply nutrients not available in the complex media. The selection scheme may involve arresting growth of the host cell. Cells, which have been successfully transformed with the genes encoding the therapeutic antibody of the present invention, survive due to e.g. drug resistance conferred by the selection marker. Another example is the so-called DHFR selection marker wherein transformants are cultured in the presence of methotrexate. In typical embodiments, cells are cultured in the presence of increasing amounts of methotrexate to amplify the copy number of the exogenous gene of interest. CHO cells are a particularly useful cell line for the DHFR selection. A further example is the glutamate synthetase expression system (Lonza Biologies). A suitable selection gene for use in yeast is the trp1 gene, see Stinchcomb et al Nature 282, 38, 1979.

4.8.4 Promoters

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression.

4.8.5 Enhancer Element

Where appropriate, e.g. for expression in higher eukaroytics, an enhancer element operably linked to the promoter element in a vector may be used. Suitable mammalian enhancer sequences include enhancer elements from globin, elastase, albumin, fetoprotein and insulin. Alternatively, one may use an enhancer element from a eukaroytic cell virus such as SV40 enhancer (at bp 100-270), cytomegalovirus early promoter enhancer, polyma enhancer, baculoviral enhancer or murine IgG2a locus (see WO04/009823). The enhancer is preferably located on the vector at a site upstream to the promoter.

4.8.6 Host Cells

Suitable host cells for cloning or expressing vectors encoding antibodies of the invention are prokaroytic, yeast or higher eukaryotic cells. Suitable prokaroytic cells include eubacteria e.g. enterobacteriaceae such as *Escherichia* e.g. *E. Coli* (for example ATCC 31, 446; 31, 537; 27,325), *Enterobacter, Erwinia, Klebsiella Proteus, Salmonella* e.g. *Salmonella typhimurium, Serratia* e.g. *Serratia marcescans* and *Shigella* as well as *Bacilli* such as *B. subtilis* and *B. lichenifonnis* (see DD 266 710), *Pseudomonas* such as *P. aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), *yarrowia* (EP402, 226), *Pichia Pastoris* (EP183, 070, see also Peng et al J. Biotechnol. 108 (2004) 185-192), *Candida, Thchoderma reesia* (EP244, 234J, Penicillin, *Tolypocladium* and *Aspergillus* hosts such as *A. nidulans* and *A. niger* are also contemplated.

Although Prokaryotic and yeast host cells are specifically contemplated by the invention, preferably however, host cells of the present invention are higher eukaryotic cells. Suitable higher eukaryotic host cells include mammalian cells such as COS-1 (ATCC No. CRL 1650) COS-7 (ATCC CRL 1651), human embryonic kidney line 293, baby hamster kidney cells (BHK) (ATCC CRL1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al., (1986) Somatic Cell Mol. Genet. 12, 555-556)), particularly those CHO cell lines adapted for suspension culture, mouse Sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NSO (see U.S. Pat. No. 5,807,715), Sp2/0, YO. Thus in one embodiment of the invention there is provided a stably transformed host cell comprising a vector encoding a heavy chain and/or light chain of the therapeutic antibody or antigen binding fragment thereof as herein described. Preferably such host cells comprise a first vector encoding the light chain and a second vector encoding said heavy chain.

4.6.1 Bacterial Fermentation

Bacterial systems may be used for the expression of non-immunoglobulin therapeutic proteins described above. Bacterial systems are also particularly suited for the expression of antibody fragments. Such fragments are localised intracellular or within the periplasma. Insoluble periplasmic proteins can be extracted and refolded to form active proteins according to methods known to those skilled in the art, see Sanchez et al (1999) J. Biotechnol. 72, 13-20 and Cu pit P M et al (1999) Lett Appl Microbiol, 29, 273-277.

4.8.7 Cell Culturing Methods

Host cells transformed with vectors encoding the therapeutic antibodies of the invention or antigen binding fragments thereof may be cultured by any method known to those skilled in the art. Host cells may be cultured in spinner flasks, roller bottles or hollow fibre systems but it is preferred for large scale production that stirred tank reactors are used particularly for suspension cultures. Preferably the stirred tankers are adapted for aeration using e.g. spargers, baffles or low shear impellers. For bubble columns and airlift reactors direct aeration with air or oxygen bubbles maybe used. Where the host cells are cultured in a serum free culture media it is preferred that the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly invertebrate host cells may utilise a variety of operational modes such as fed-batch, repeated batch processing (see Drapeau et al (1994) cytotechnology 15: 103-109), extended batch process or perfusion culture. Although recombinantly transformed mammalian host cells may be cultured in serum-containing media such as fetal calf serum (FCS), it is preferred that such host cells are cultured in synthetic serum-free media such as disclosed in Keen et al (1995) Cytotechnology 17:153-163, or commercially available media such as ProCHO-CDM or Ultra-CHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in Animal Cell technology: Developments towards the 21st century (Beuvery E. G. et al eds), pp 619-623, Kluwer Academic publishers).

Antibodies or other therapeutic proteins of the invention secreted into the media may be recovered and purified using a variety of techniques to provide a degree of purification suitable for the intended use. For example the use of therapeutic antibodies of the invention for the treatment of human patients typically mandates at least 95% purity, more typically 98% or 99% or greater purity (compared to the crude culture medium). In the first instance, cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429, 746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (preferably monoclonal) preparation comprising at least 75 mg/ml or greater e.g. 100 mg/ml or greater of the antibody of the invention or antigen binding fragment thereof is provided and therefore forms an embodiment of the invention. Suitably such preparations are substantially free of aggregated forms of antibodies of the invention.

4.9 Screening Methods

In other embodiments there is provided a method of/for identifying modulators of the interaction between 7,25DHC and/or 7,27DHC and/or 7HC and/or 25HC and EBI2. Such method generally comprise bringing into contact 7,25DHC and/or 7,27DHC and/or 7HC in the presence of a candidate compound and observing a modulation (such as inhibition) of the interaction between either or both of the ligands 7,25DHC and/or 7,27DHC and/or 7HC and/or 25HC and EBI2 compared to the same experiments in absence of the candidate compound. In preferred embodiments of the invention, the ligands are 7a,25DHC and/or 7b,25DHC and/or 7a,27DHC and/or 7b,27DHC and/or 7aHC and/or 7bHC and/or 25HC. Candidate compounds that exhibit inhibition characteristics may be further structurally modified to improve IC50 against its target entity and/or improve toxicity profile prior to formulation and administering to a human patient in clinical need thereof.

4.10 Pharmaceutical Compositions

The invention provides pharmaceutical compositions comprising the therapeutic protein or low molecular weight chemical entity formulated together with a pharmaceutically acceptable carrier. The compositions can additionally contain other therapeutic agents that are suitable for treating or preventing a human disease or disorder noted below. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound (particularly low molecular weight chemical entities) may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the modulator of NRG1 (e.g. NRG1β1) such as a NRG1β1 antibody described herein is employed in the pharmaceutical compositions of the invention. They are typically formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

Antibody and other protein therapeutics are usually administered on multiple occasions. Intervals between single dosages can be weekly, monthly or yearly. Intervals can also be irregular as indicated by measuring blood levels of therapeutic protein in the patient. In some methods, dosage is adjusted to achieve a plasma antibody concentration of 1-1000 μg/ml and in some methods 25-300 μg/ml. Alternatively, antibody or other protein therapeutics can be administered as a sustained release formulation, in which case less frequent administration is required. Dosage and frequency vary depending on the half-life of the antibody or other protein therapeutic in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Thus the invention concerns a pharmaceutical composition comprising a modulator of the interaction between 7,25DHC and/or 7,27DHC and/or 7HC and/or 25HC and EBI2 together with a pharmaceutically acceptable carrier or diluent. In a preferred embodiment, pharmaceutical composition comprising a modulator of the interaction between 7a,25DHC and/or 7b,25DHC and/or 7a,27DHC and/or 7b,27DHC and/ or 7aHC and/or 7bHC and/or 25HC and EBI2. Typically such modulators are inhibitors as described hereinbefore.

4.11 Clinical Uses

Pharmaceutical compositions of the invention comprises modulators, particularly inhibitors of the interaction between 7,25DHC and/or 7,27DHC and/or 7HC and/or 25HC and EBI2, preferably inhibitors of the interaction between 7a,25DHC and/or 7b,25DHC and/or 7a,27DHC and/or 7b,27DHC and/or 7aHC and/or 7bHC and/or 25HC and EBI2, maybe used in diseases or disorders responsive to the modulation of this interaction. Examples of such diseases include hypertension, angina pectoris, atherosclerosis, congestive heart failure, stroke, obesity, metabolic syndrome, autoimmune diseases such as arthritis, (especially rheumatoid arthritis), multiple sclerosis, and lupus, as well as atopic conditions such as asthma and atopic dermatitis, COPD, pulmonary hypertension, viral infections such as EBV, HIV, hepatitis (A or C), fatty liver disease, liver sclerosis (particularly alcohol induced liver sclerosis), cancer, dyslipidemia, diabetes (particularly type II), transplant rejection, irritable bowel syndrome, inflammatory bowel disease, diseases of chronic inflammation, allergy, psoriasis, cystic fibrosis, hypercholesterolaemia, renal disease.

5. EXEMPLIFICATION

The present invention is now described by way of example only.

In the figures:

FIG. 1: flow cytometry analysis of hEBI2 plasma membrane expression in hEBI2 CHO-Aeq clones versus wild type CHO-Aeq.

Figure 2:
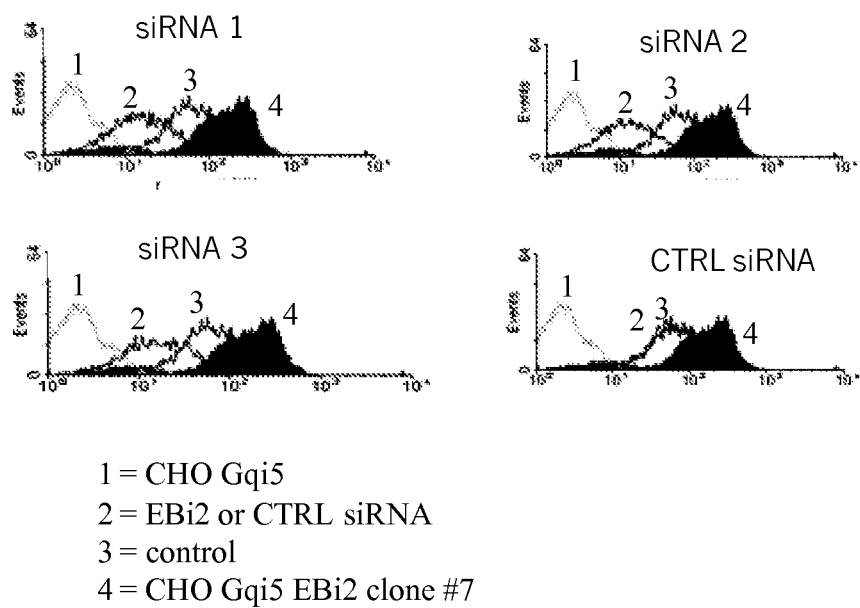

FIG. 2: Decrease in plasma membrane expression of hEBI2 in CHO-Aeq cells after transient transfection (Lipofectamin) of EBI2-specific siRNA oligonucleotides.

Figure 3:
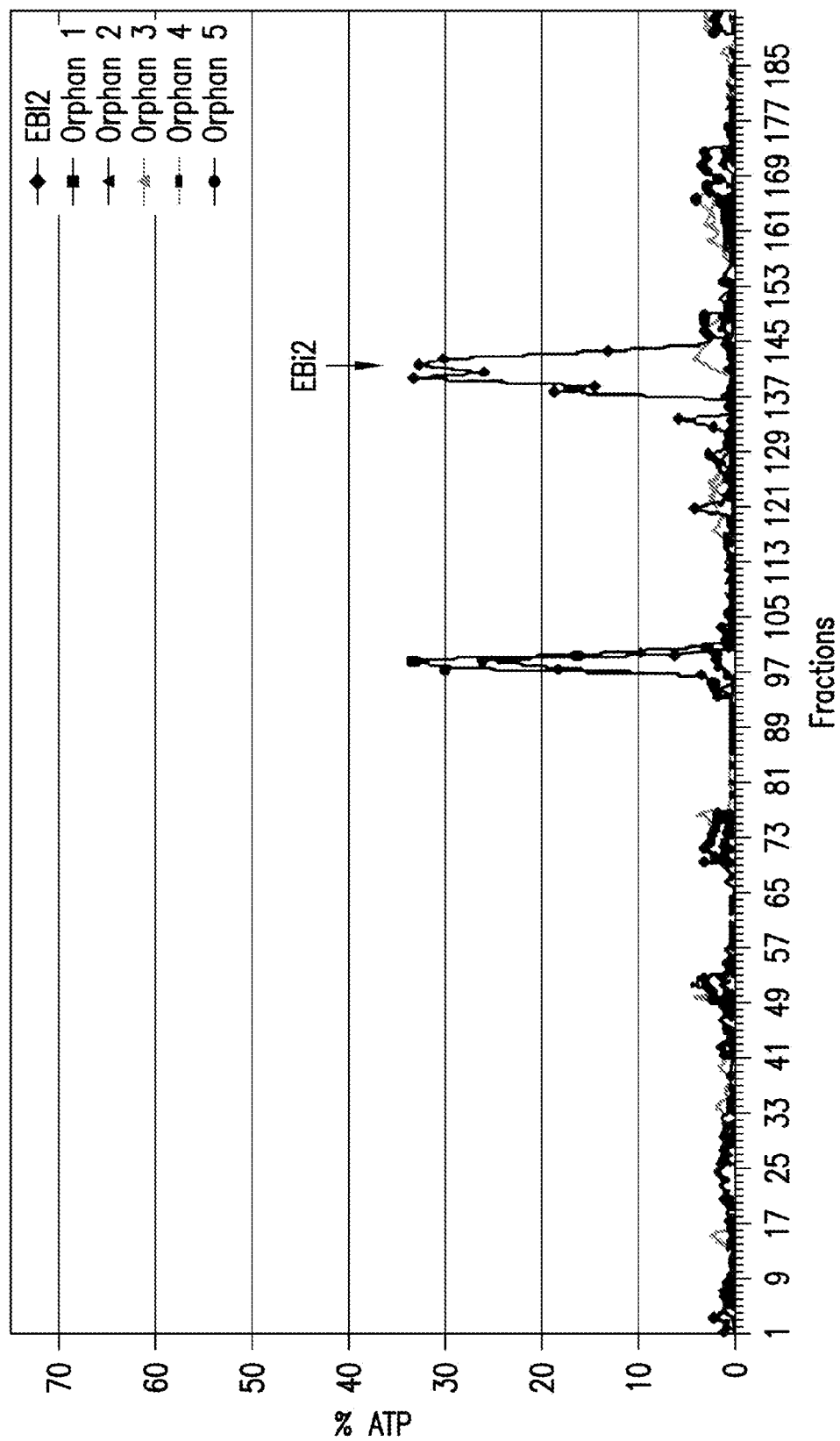

FIG. 3: Identification of specific EBI2 "activity" in a human septic liver extract during an aequorin primary screening. X axis=fraction number, Y axis=% ATP in increasing divisions of 10%.

Figure 4:
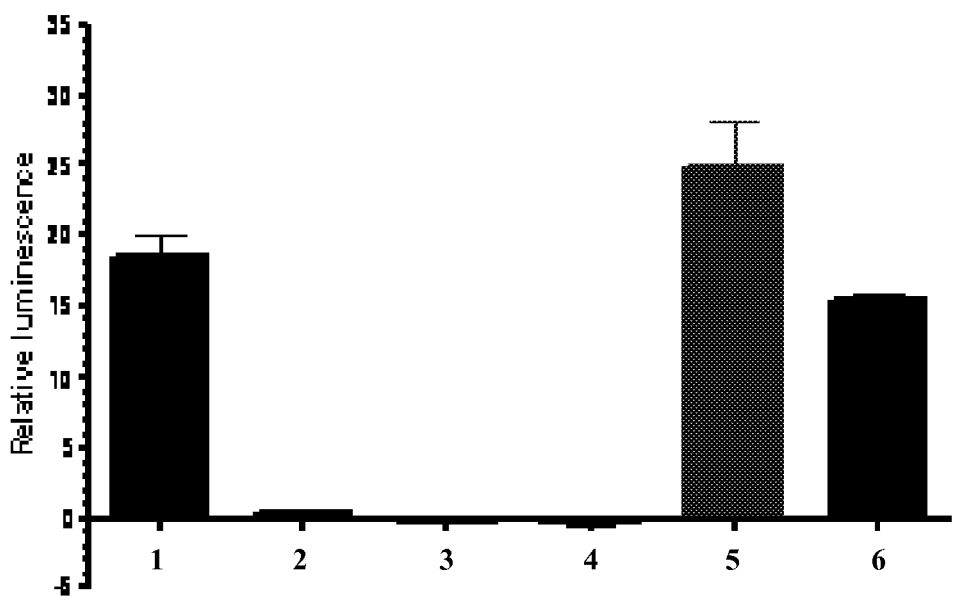

FIG. 4: Decrease of hEBI2 activation with human liver extract, after transient transfection of EBI2 siRNAs (SeqIDs as defined in Table 2 below) in hEBI2-CHO-AeqGqi5 cells. From the left to the right:
1. EBI2 clone 7;
2. EBI2 clone 7+SiRNA 1
3. EBI2 clone 7+SiRNA 2
4. EBI2 clone 7+SiRNA 3
5. EBI2 clone 7+SiRNA 4 (control)
6. EBI2 clone 7 control (lipo)

Figure 5:
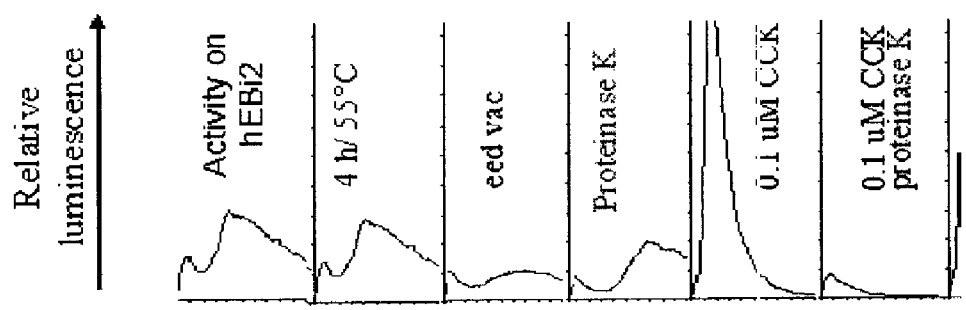

FIG. 5: Activation of hEBI2 (aequorin) with active liver fractions treated or not with Proteinase K.

Figure 6:
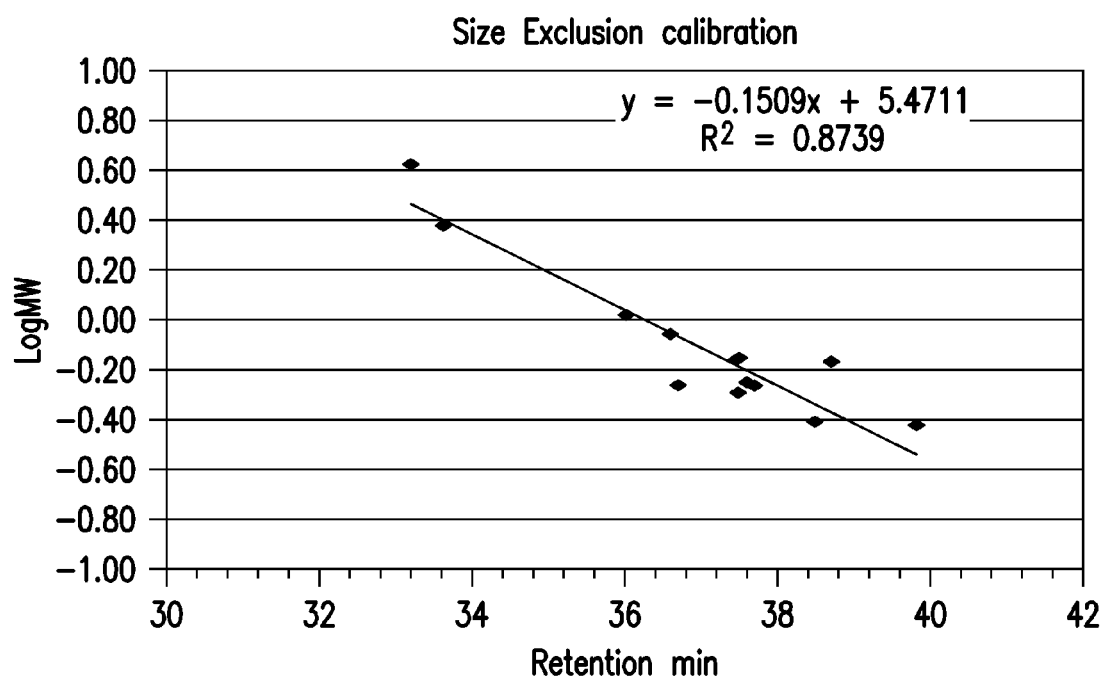

FIG. 6: Determination of molecular size of EBI2 ligand using active liver fractions and size exclusion chromatography.

Figure 7:
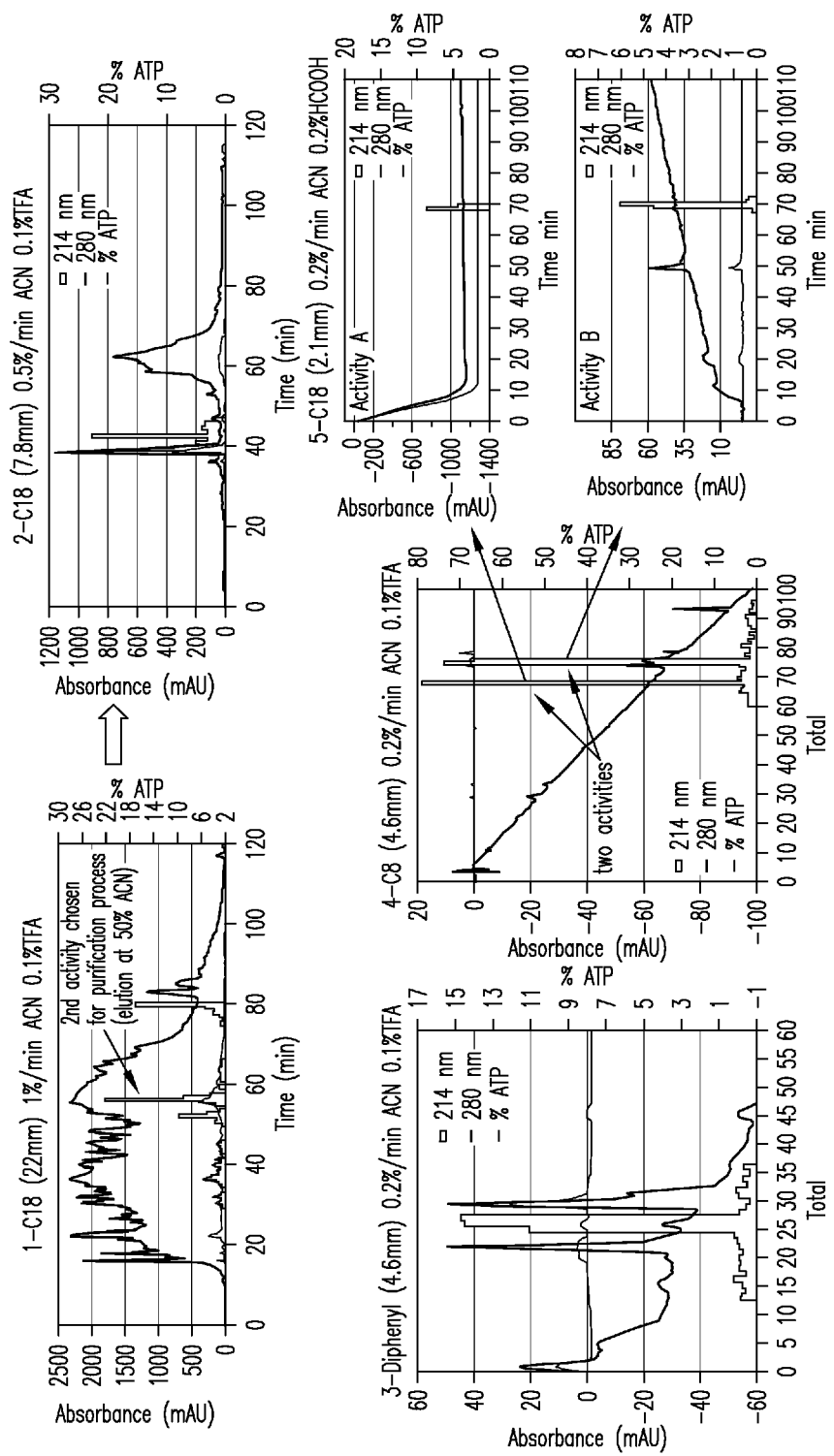

FIG. 7: Purification of hEBI2 natural ligand from human septic liver extract: 5 step liquid chromatography procedure.

Figure 8:
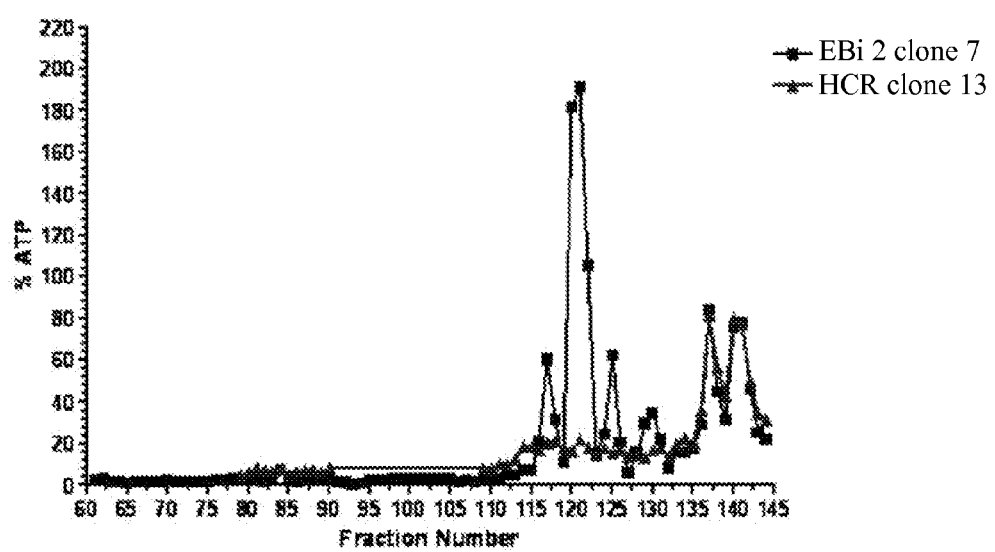
Figure 9A:
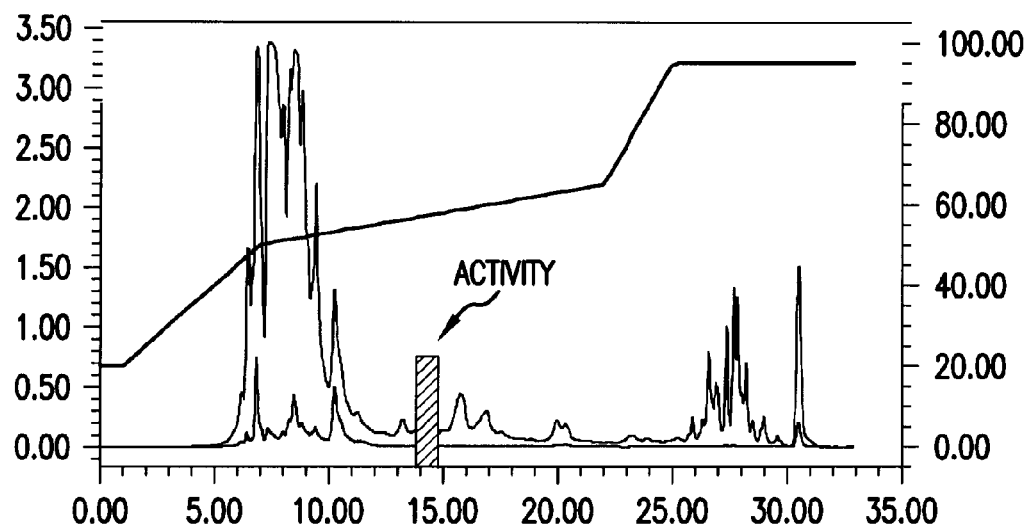
Figure 9B:
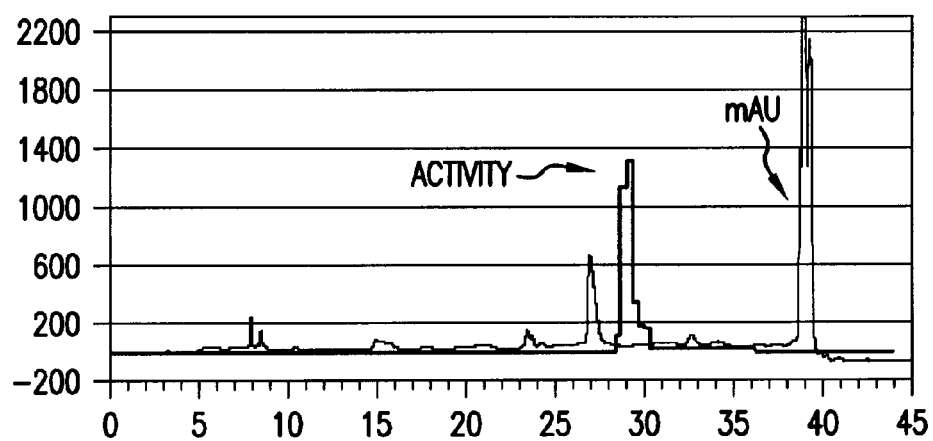
Figure 9C:
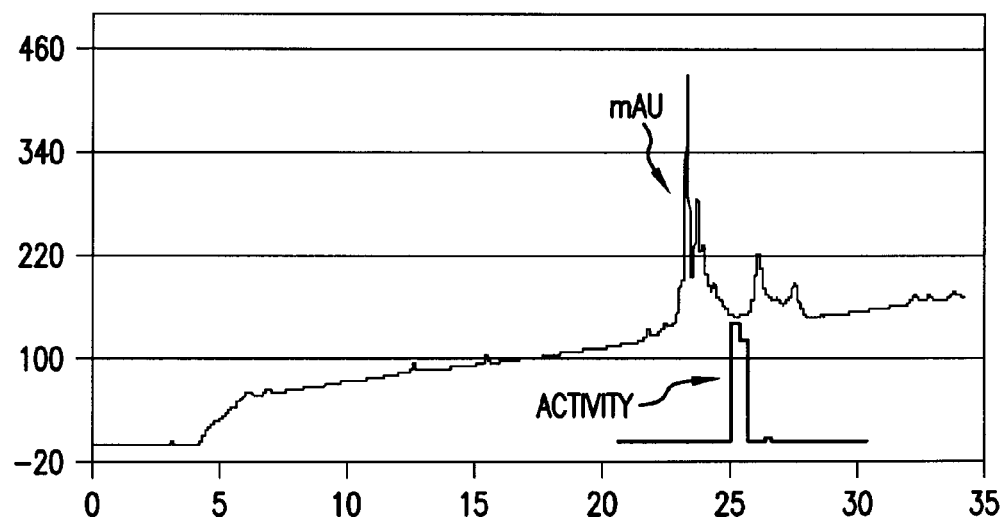
Figure 9D:
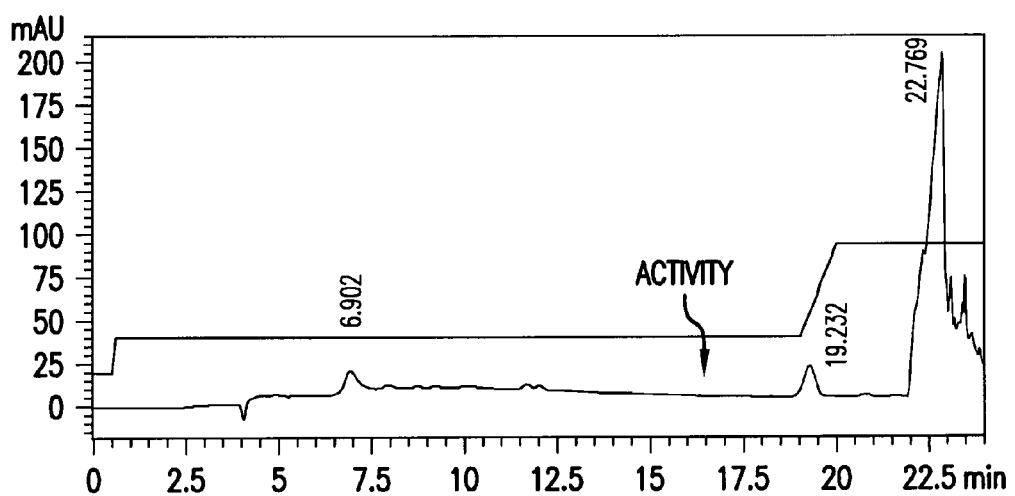
Figure 9E:
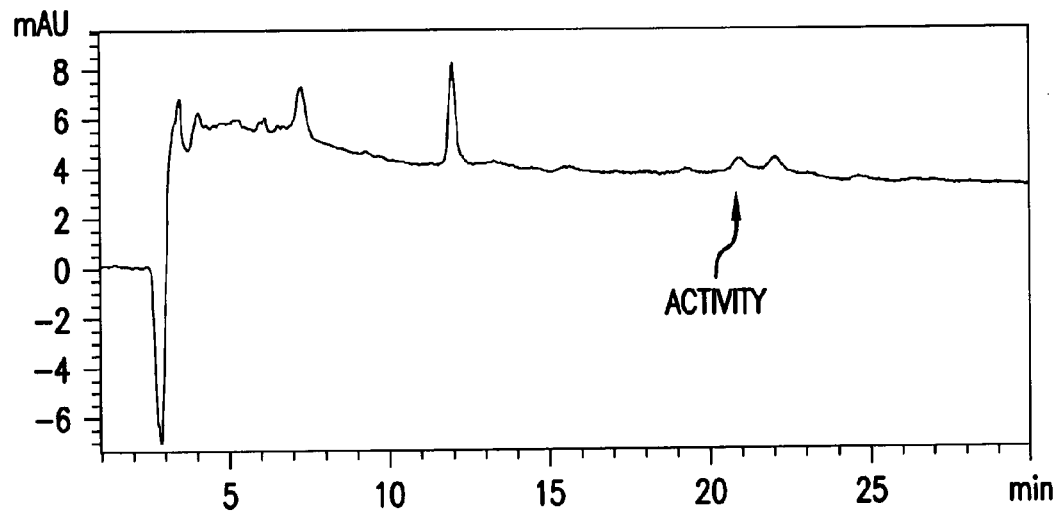
Figure 9F:
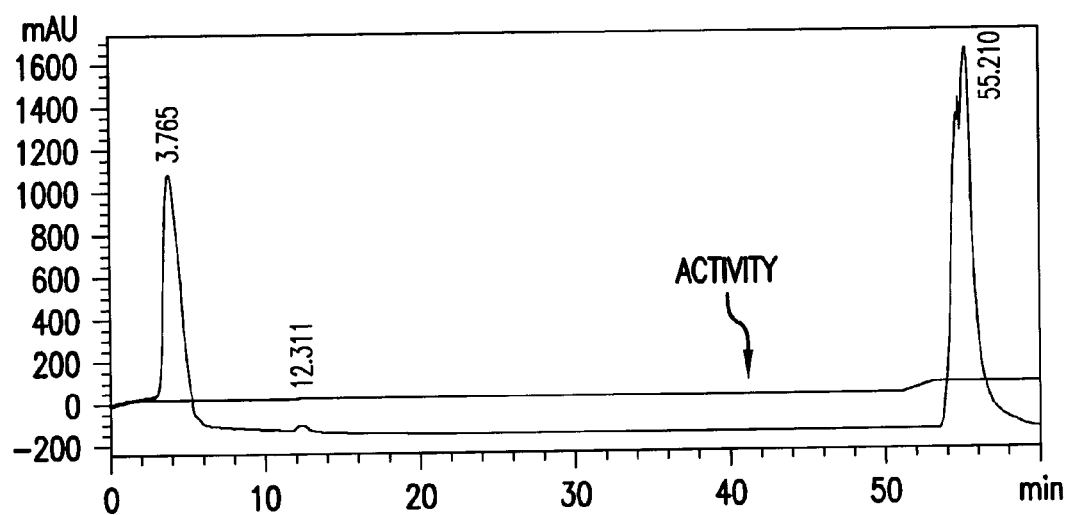

FIG. 8: Aequorin screening of hEBi-CHO-AeqGqi5 clone 7 on a liver extract from a sheep sepsis model.

FIG. 9: Purification of hEBI2 natural ligand from sheep septic liver extract with six successive liquid chromatography steps. X-axis=time (in minutes); Y-axis=AU (absorption units) (A) or mAU (milli-absorption units) (B-F,). Step 1 corresponds to panel (A); step 2 to (B); step 3 to (C); step 4 to (D); step 5 to (E) and step 6 to (D). In steps 4 panel (D) the activity is detected between 16.25 and 16.75 min (not shown in the Figure). In steps 5 panel (E) the activity is detected between 20.50 and 21.50 min (not shown in the Figure). In steps 6 panel (F) the activity is detected between 39 and 40 min (not shown in the Figure).

Figure 10:
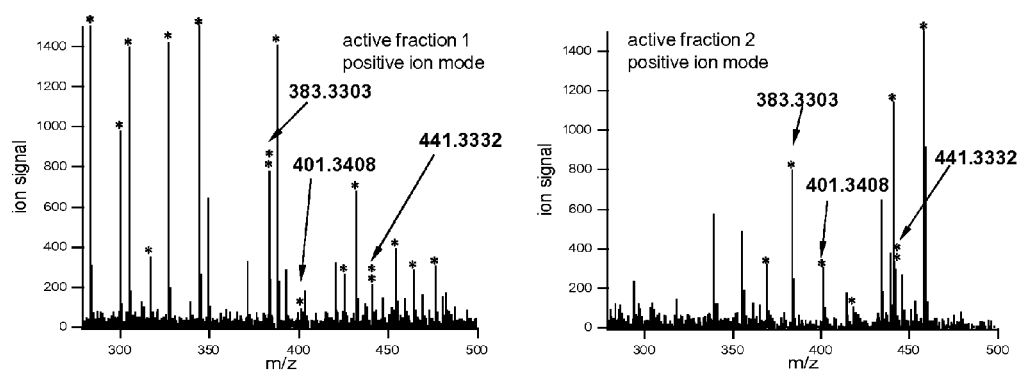
Figure 10:
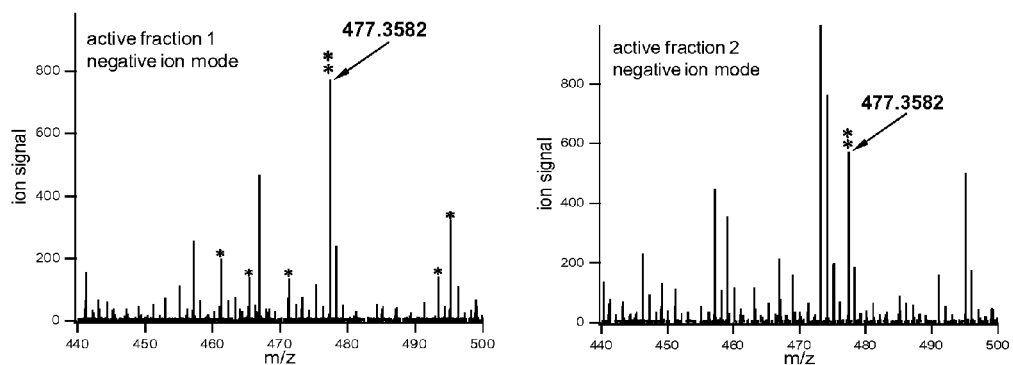

FIG. 10: MS analysis of EBI2 active and control fractions in positive and negative ion modes (Nano ESI-FTMS, Orbitrap). (*) indicates peaks detected only in the active fraction (vs. control fraction) whilst (**) indicates common peaks in two active fractions collected by different LC methods.

Figure 11:
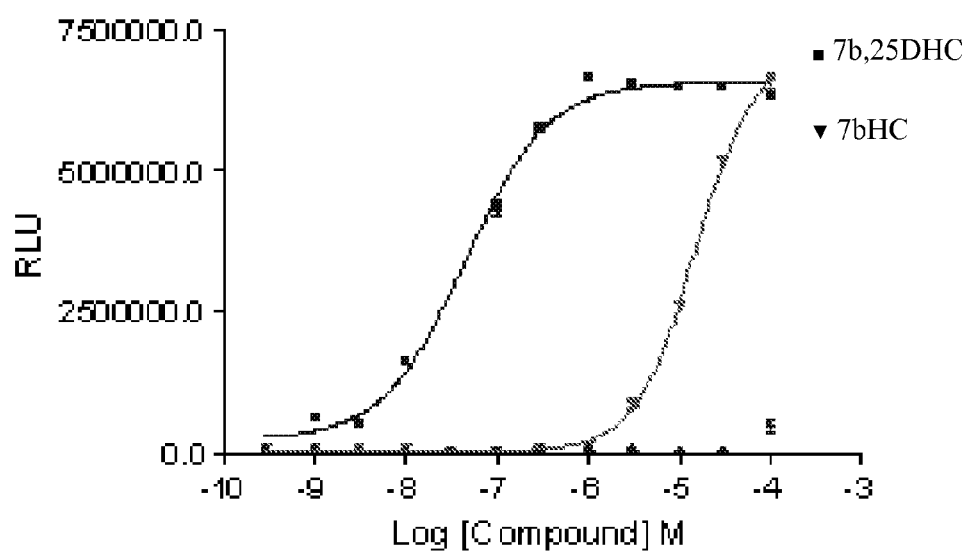

FIG. 11: 7b,25DHC and 7bHC activate hEBI2 stably expressed in a CHO-AeqGqi5 (aequorin).

Figure 12:
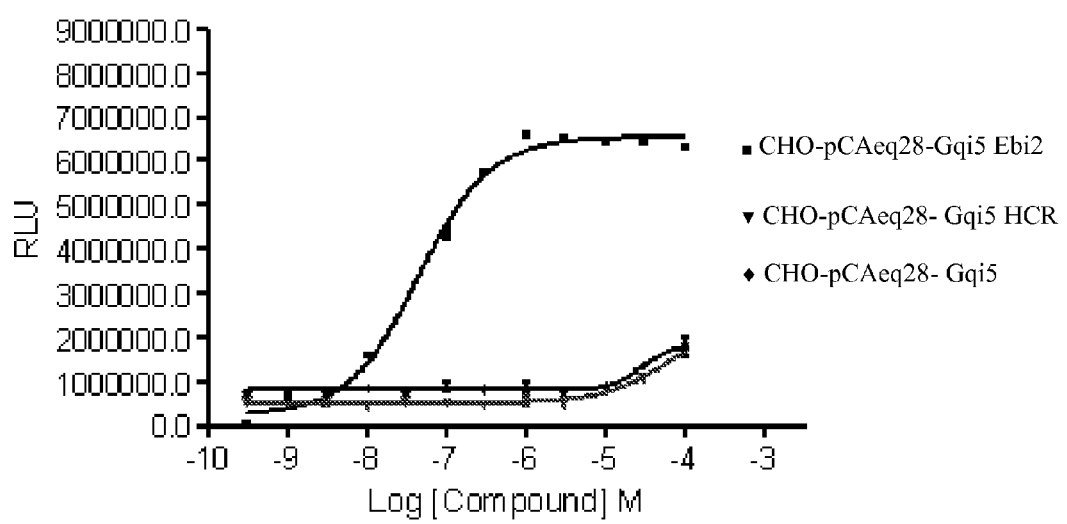

FIG. 12: Activation of human EBI2 stably expressed in CHO-AeqGqi5 cells with 7b,25DHC is specific (aequorin assay).

Figure 13:
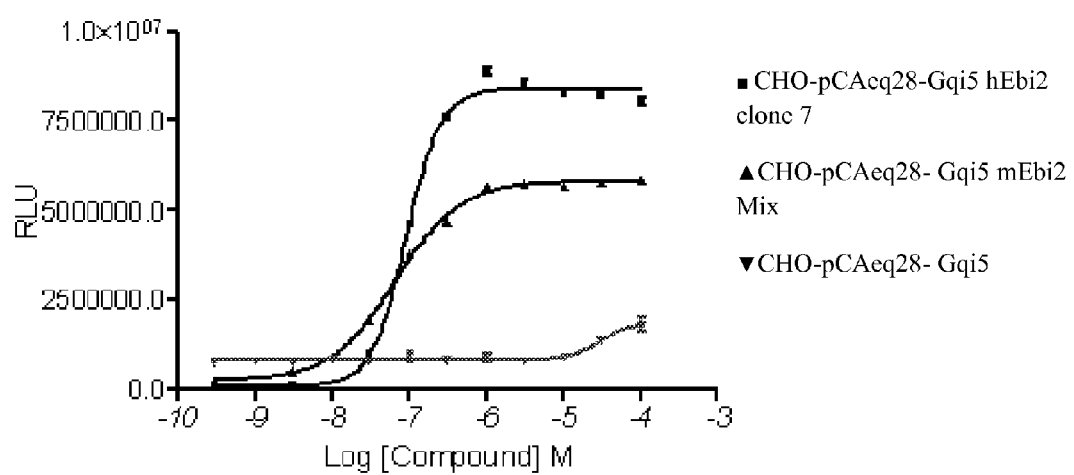

FIG. 13: Activation of human and mouse EBI2 with 7b,25DHC confirmed in different hEBI2 CHO-AeqGqi5 cell lines (aequorin assay).

Figure 14:
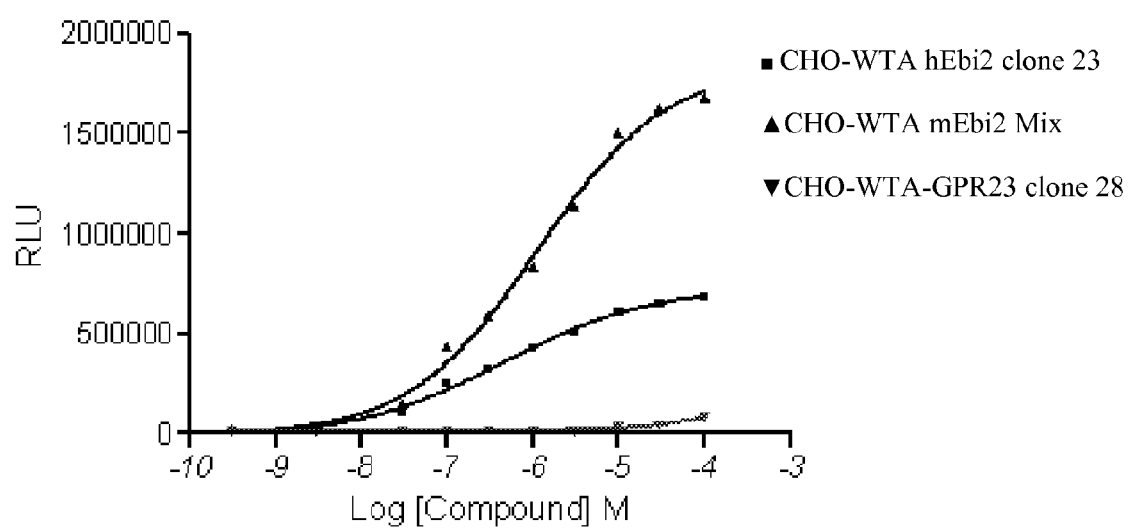

FIG. 14: Activation of human and mouse EBI2 stably expressed in CHO-Aeq Gα16 cells with 7b,25DHC (aequorin assay).

Figure 15:
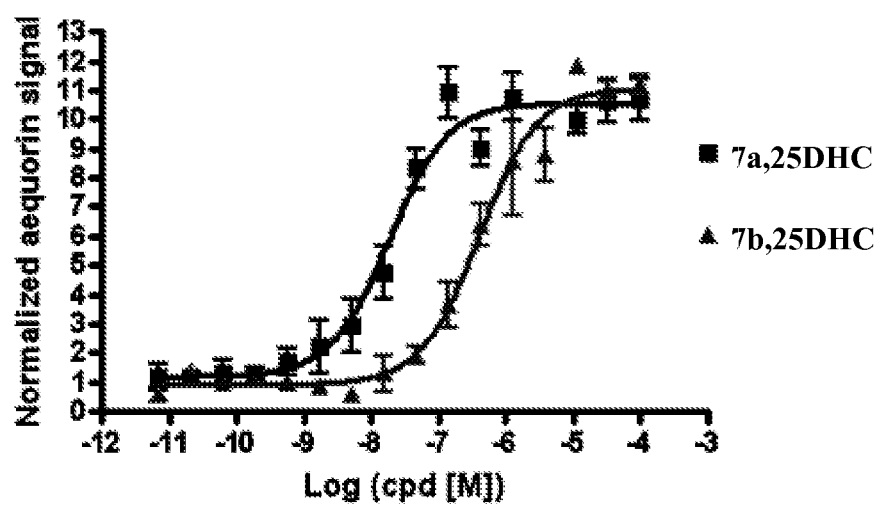

FIG. 15: Aequorin assay to measure the activation of hEBI2 by 7a,25DHC and 7b,25DHC in stably transfected CHO-AeqGα16 cells.

Figure 16:
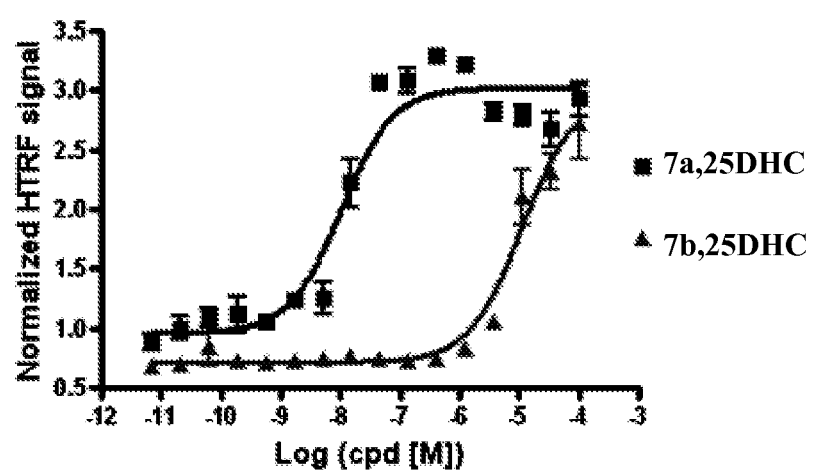

FIG. 16: cAMP assay to measure the activation of hEBI2 by 7a,25DHC and 7b,25DHC in stably transfected CHO-AeqGα16 cells.

Figure 17:
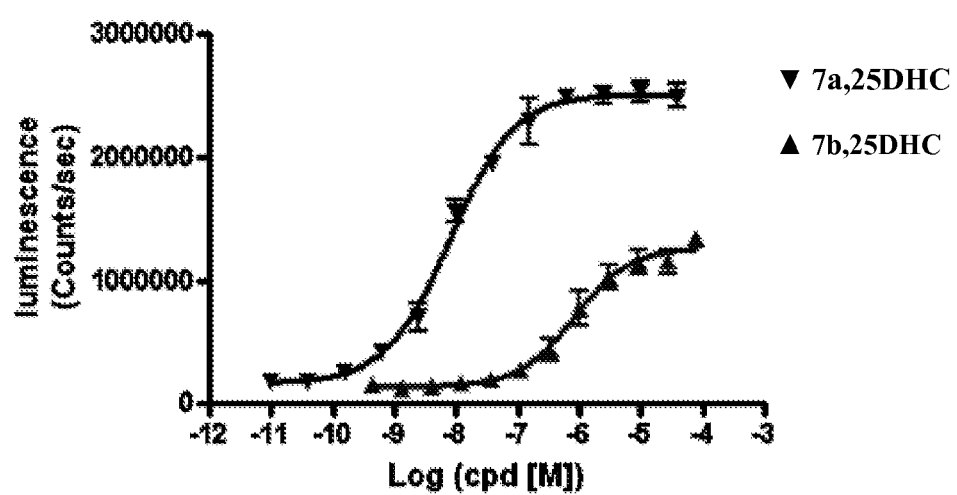

FIG. 17: β-arrestin Pathhunter assay to assess activation of hEBI2 by 7a,25DHC and 7b,25DHC.

Figure 18:
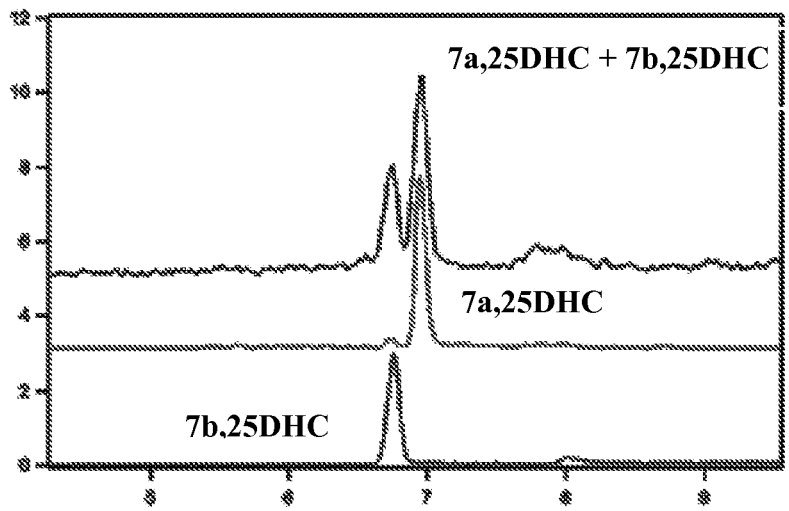
Figure 18:
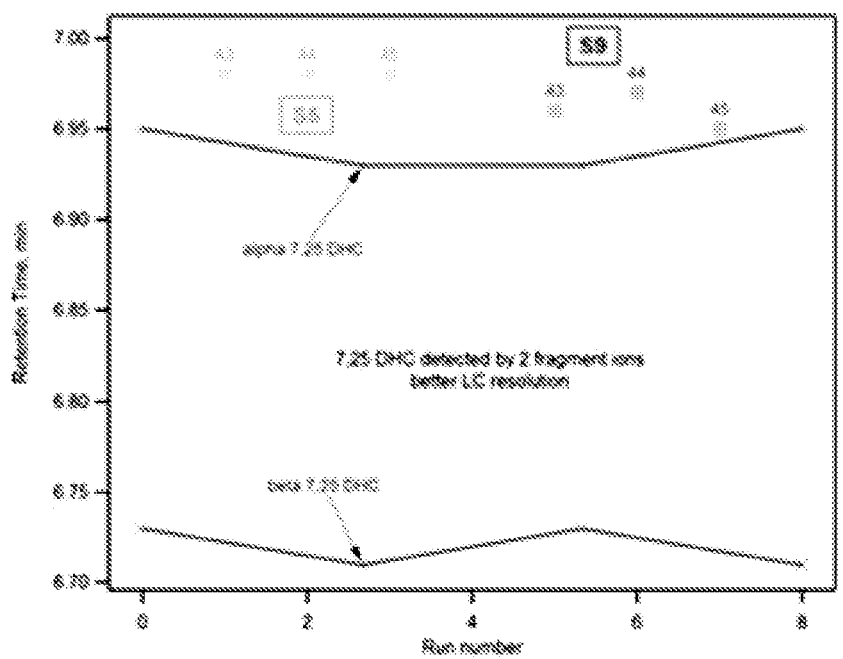

FIG. 18: (A) Liquid chromatography to separate 7a,25DHC from 7b,25DHC. (B) Retention time matching of six different active fractions.

Figure 19:
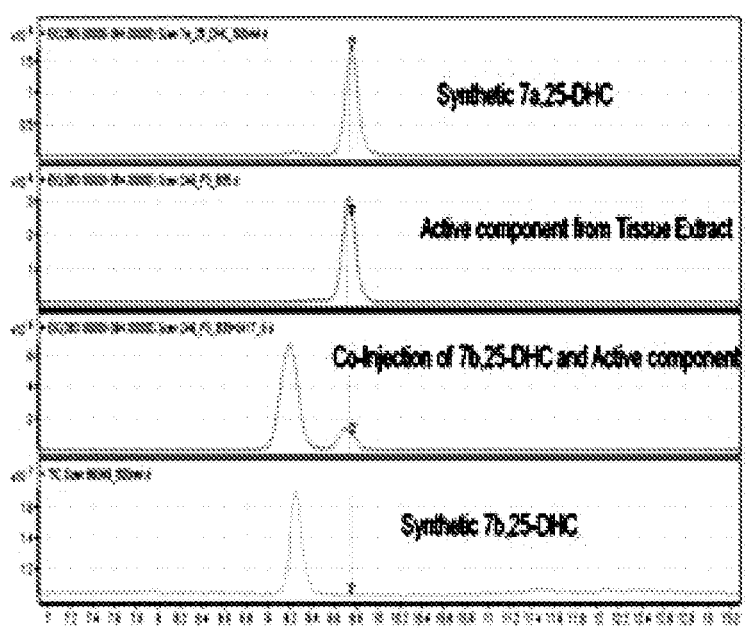

FIG. 19: Liquid Comparison of retention times of EBI2 natural ligand with synthetic 7a,25DHC and 7b,25DHC (count vs acquisition time).

FIG. 20: $^1$H-NMR of (A) synthetic 7a,25DHC and (B) isolated EBI2 natural ligand from pig liver.

Figure 21:
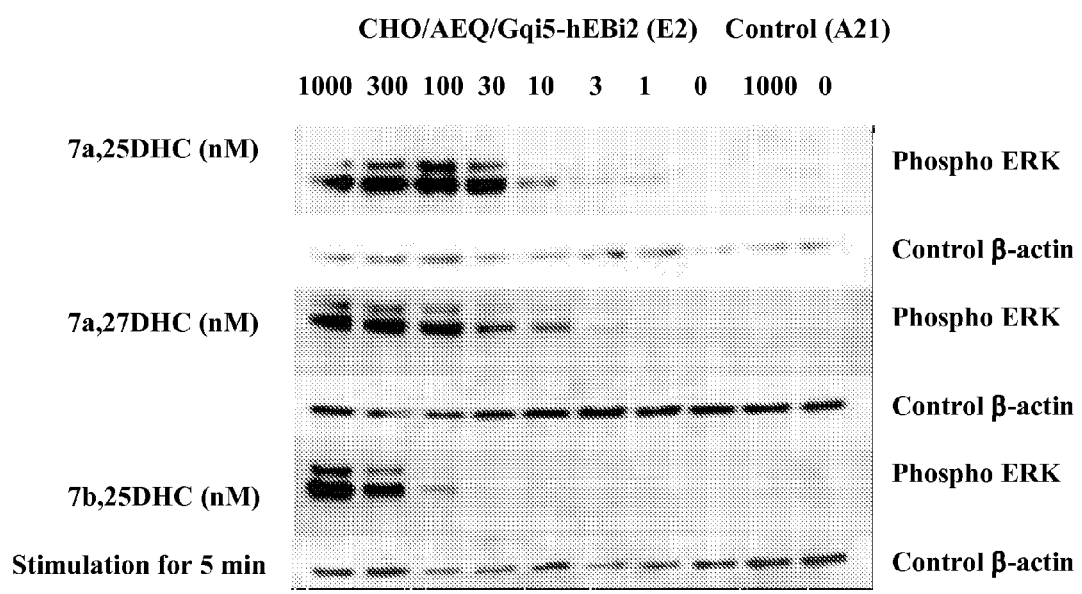

FIG. 21: Western blot analysis of MAP/ERK phosphorylation 5 minutes after EBI2 activation by different oxysterols using a phospho p44/42 MAPK specific antibody.

Figure 22:
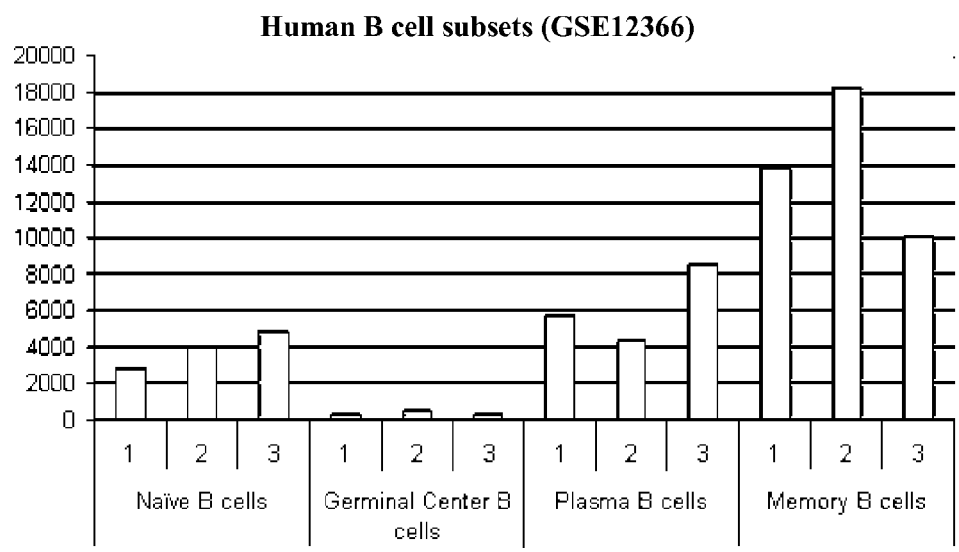
Figure 22:
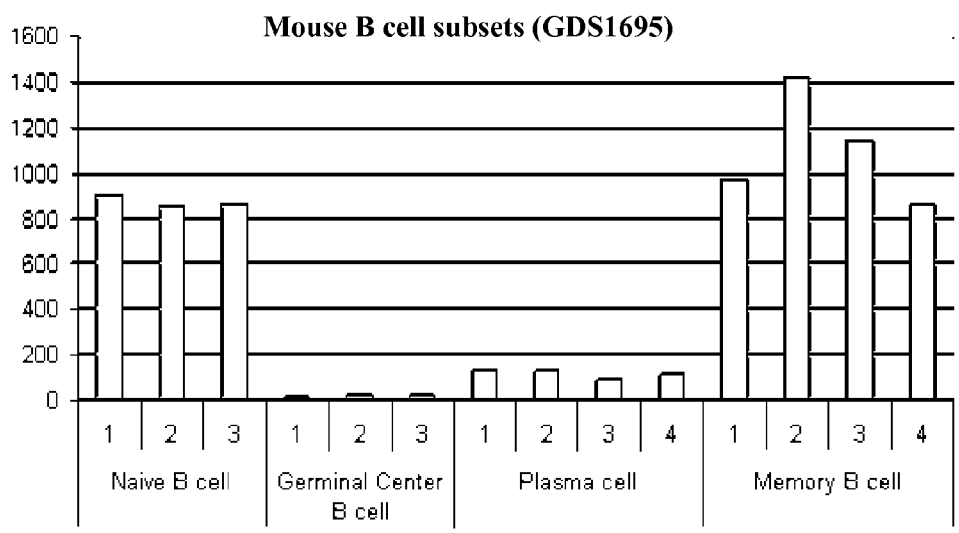

FIG. 22: DNA array analysis of (A) human EBI2 and (B) mouse EBI2 in different B cells subsets.

Figure 23:
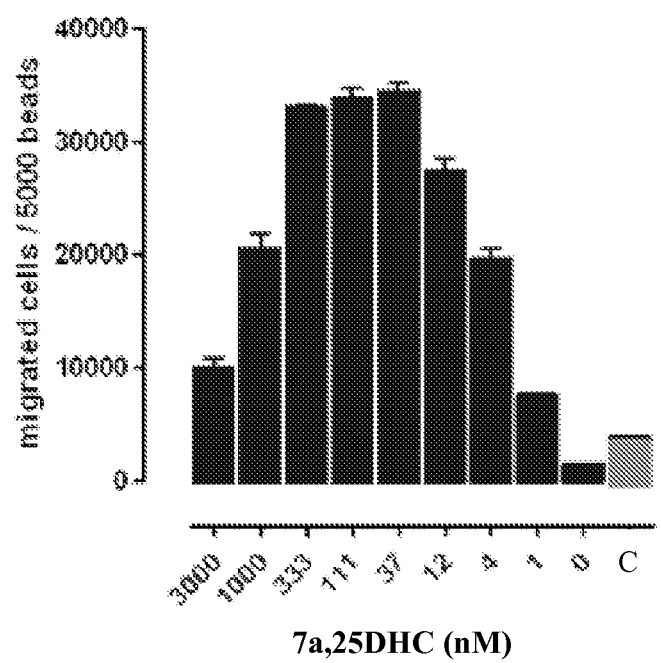

FIG. 23: Migration of EBV-infected human B cells towards 7a,25DHC.

Figure 24:
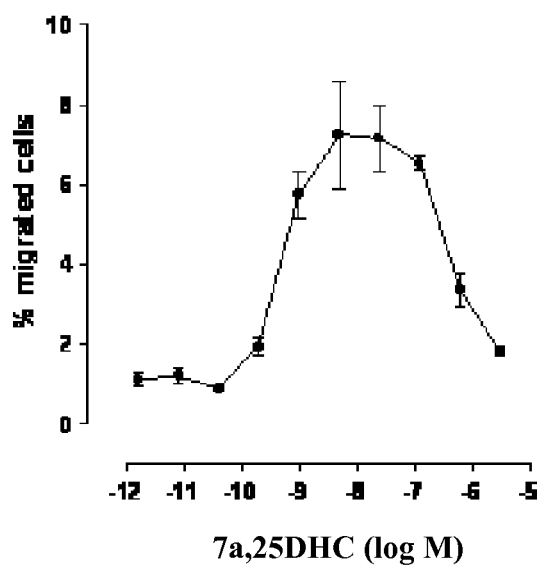
Figure 24:
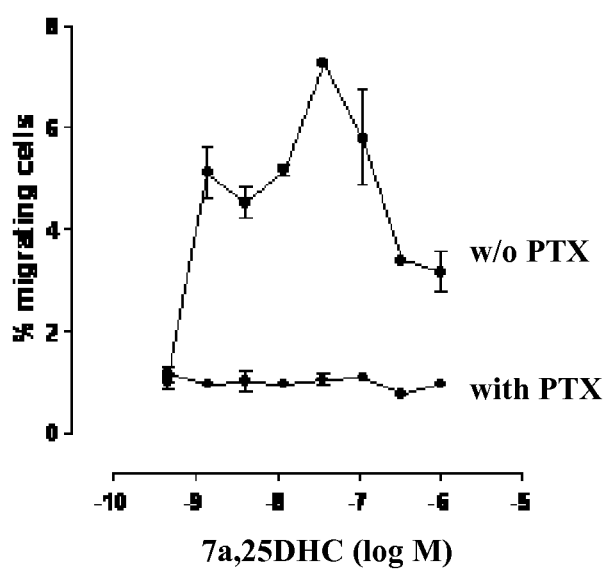

FIG. 24: (A) Migration of RS11846 cells towards 7a,25DHC in a 96 transwell assay. (B) Inhibition of oxysterol-mediated chemotaxis of RS11846 cells by pertussis toxin (PTX).

Figure 25:
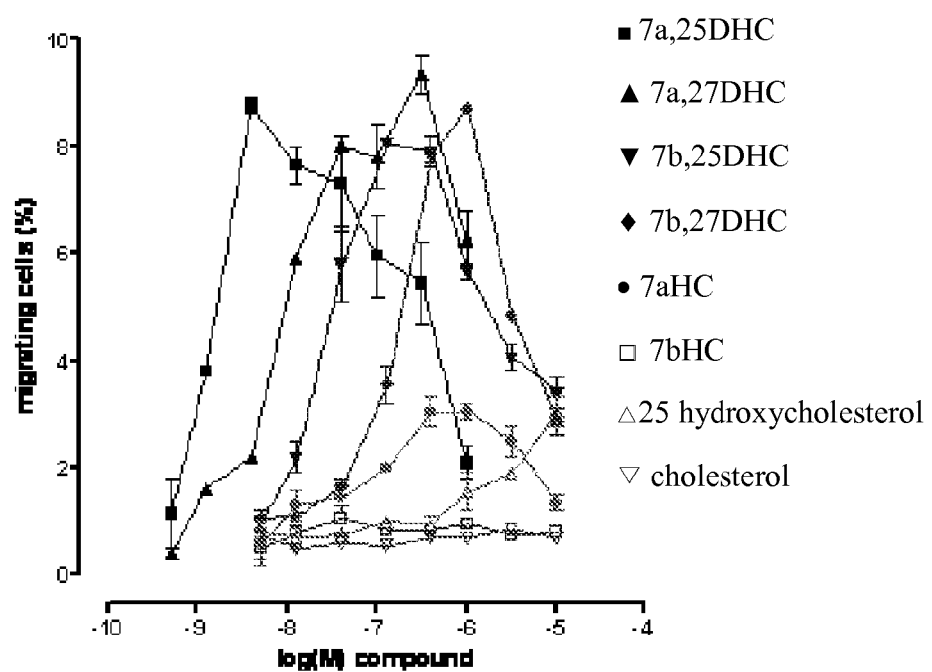

FIG. 25: Migration of RS11846 cells towards different oxysterols.

Figure 26:
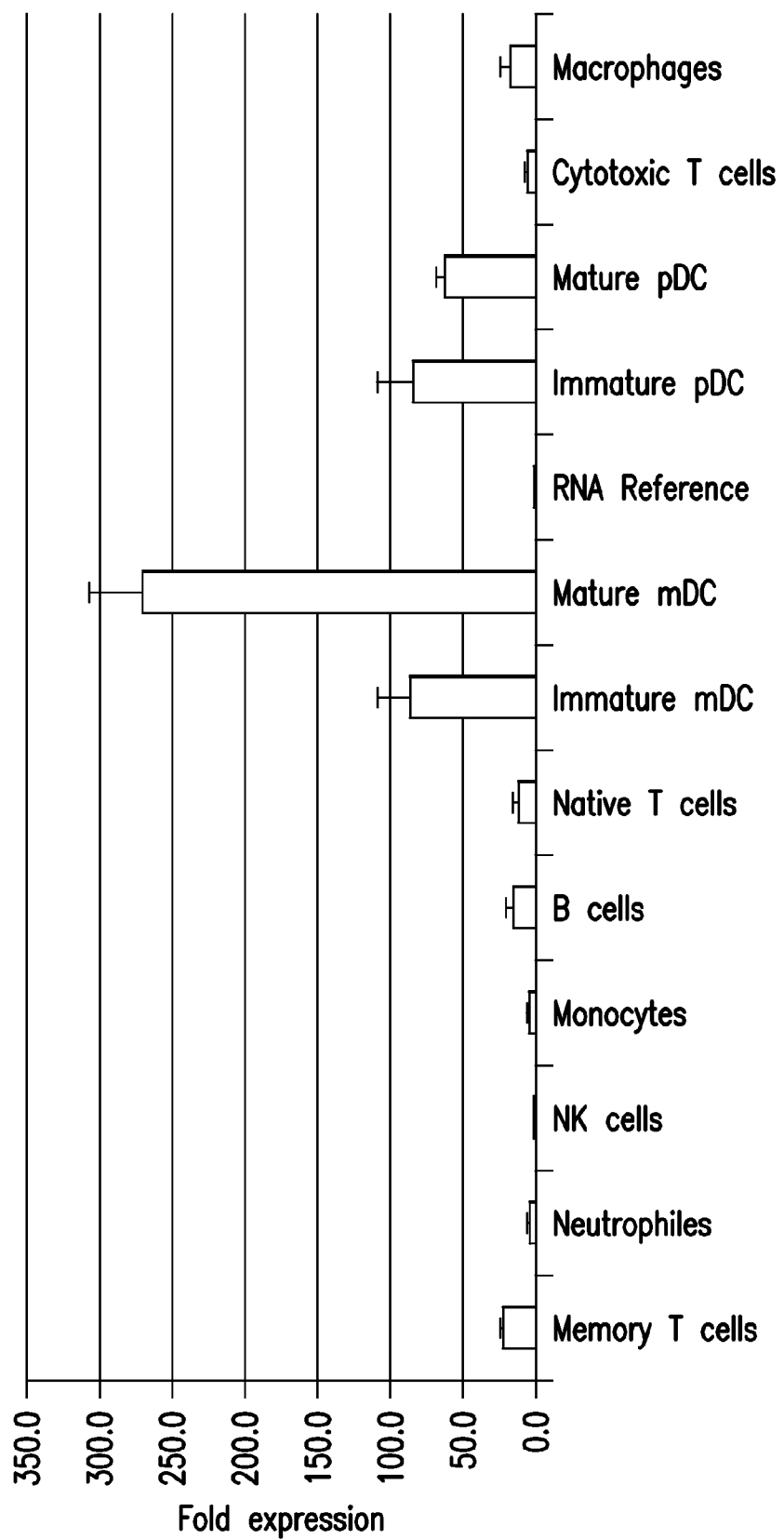

FIG. 26: Q-PCR profiling of EBI2 mRNA expression level in human immune cells.

Figure 27:
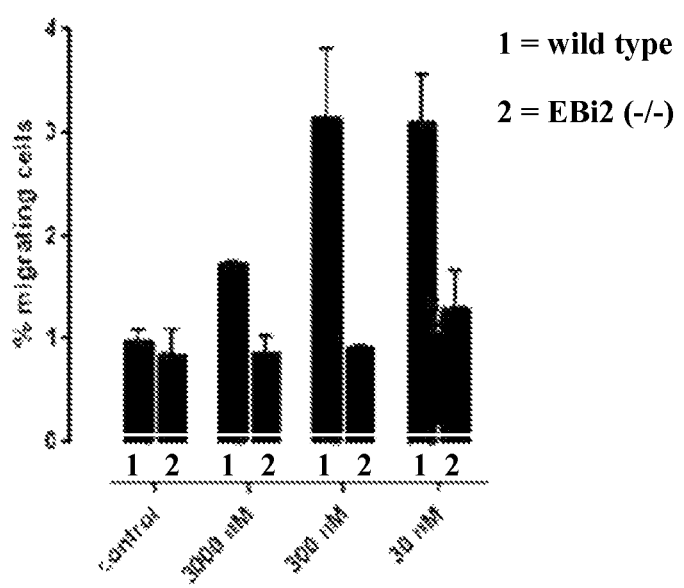

FIG. 27: 7a,25DHC-mediated cell migration of mouse bone marrow-derived dendritic cells.

Figure 28:
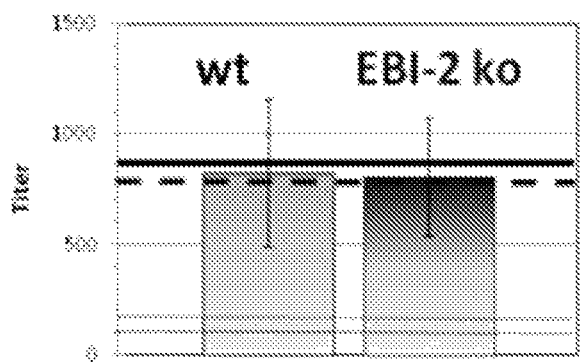
Figure 28:
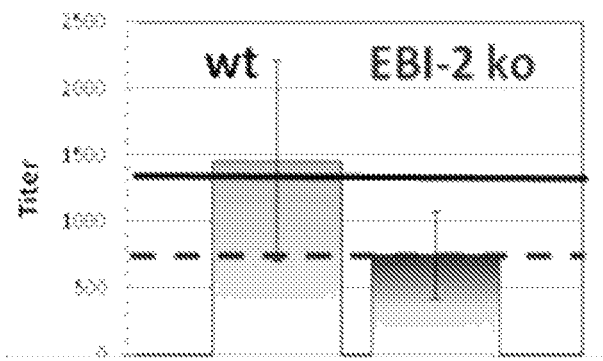

FIG. 28: NP-CGG challenge of wild type and EBI2 (−/−) mice. (A) anti-NP IgM serum titers and (B) anti-NP IgG1 serum titer after 7 days.

5.1 EBI2 Recombinant Cell Lines

Human EBI2 gene was cloned using RT-PCR from HL-60 cDNA and corresponded to the Genbank accession number NP_004942. The human EBI2 was inserted into the pEFIN3 vector at the EcoRI and XbaI sites in the multiple cloning site. Mouse EBI2 was cloned using RT-PCR from mouse genomic DNA and corresponded to the Genbank accession number Q3U6B2. The mouse EBI2 was inserted into the pEFIN3 vector at the EcoRI and XbaI sites in the multiple cloning site. Plasmids expressing human and mouse EBI2 were stably transfected in CHO-K1 and HEK293 cells expressing the apoaequorin (CHO-Aeq and HEK-Aeq) (Table 1). mRNA sequence integrity of EBI2 gene was checked using RT-PCR at T0 & T30 culture times in CHO cells.

TABLE 1

Human and mouse EBI2 recombinant aequorin cell lines.

| | Parental cell lines | G protein | Pool (mix) | Clones |
|---|---|---|---|---|
| Human EBI2 | CHO-Aeq | Gα16 | x | #23 |
| | CHO-Aeq | Gqi5 | x | #7 |
| | CHO-Aeq | — | x | |
| | HEK-Aeq | Gα16 | x | |
| Mouse EBI2 | CHO-Aeq | Gα16 | x | |
| | CHO-Aeq | Gqi5 | x | |
| | CHO-Aeq | — | x | |

5.2 Human EBI2 Monoclonal Antibody

A hEBI2 monoclonal antibody (Costagliola, S., et al. (2000). Genetic immunization of outbred mice with thyrotropin receptor cDNA provides a model of Graves' disease. J. Clin. Invest 105, 803-811) was used to verify stable plasma membrane expression of hEBI2 in recombinant CHO cells using flow cytometry (FIG. 1).

5.3 Human EBI2 siRNA

Three different siRNA oligonucleotide sequences specific for hEBI2 were developed and validated (Table 2). The 'silencing' action of these siRNA on hEBI2 gene expression was validated after siRNA transient transfection in hEBI2-CHO-Aeq cells, using flow cytometry. A significant decrease of hEBI2 receptor expression at the cell surface is observed after cells treatment with hEBI2 siRNA (FIG. 2).

TABLE 2 hEBI2 specific siRNA oligonucleotide sequences

| siRNA | receptor | siRNA sequence (5'-3') | SEQ.I.D.NO: |
|---|---|---|---|
| 1 | EBI2 | GAAGCUUCGUUUCUCUAAU | 1 |
| 2 | EBI2 | GCAGGAGGCUGAAAGGAUU | 2 |
| 3 | EBI2 | GUCAGUGUAUCGAUUUCUA | 3 |
| 4 | Ctrl | CAUGCUAUCUGCCAGAAAU | 4 |

5.4 Specific Activation of hEBI2 with Fractions from Human Septic Liver Extract hEBI2 CHO-Aeq cell lines were screened in a luminescent aequorin functional assay against proprietary libraries of natural ligands and collection of tissue extracts. We identified specific activation of hEBI2 with fractions from a human septic liver (FIG. 3).

The detailed activation profile of EBI2 against this pathological liver extract displayed three activity peaks eluted within 48%, 50% et 60% acetonitrile, respectively. These 'biological activities' could be identified in pathological liver conditions (sepsis) but normal liver extracts did not activate EBI2.

5.5 Specificity of EBI2 Activation with Human Liver Extract

Before initiating the purification of hEBI2 ligand from liver tissue extracts, it was necessary to confirm the specificity of hEBI2 activation and discriminate it from any putative CHO cells endogenous response. To this aim, we selectively down-regulated the expression of hEBI2 gene with the use of specific hEBI2 siRNA oligonucleotide sequences. We observed a consecutive decrease of EBI2 activation with human liver extract upon transient transfection of hEBI2 siR-NAs (SeqIDs as shown in Table 2) in hEBI2-CHO-AeqGqi5 cells (FIG. 4).

Physico-Chemical Properties and Molecular Size of Ebi2 Ligand.

EBI2 specific 'activity' did not decrease after treatment with proteinase K suggesting that EBI2 ligand is not a peptide (FIG. 5).

Molecular Size of Ebi2 Ligand

Molecular size of EBI2 ligand was estimated using active liver fractions and size exclusion chromatography. Estimated size for EBI2 ligand was around 400 Daltons (FIG. 6).

MS Analysis of Active Human Liver Fractions

1-LC-MS analyses of active human liver fractions were performed on a Waters HPLC (Ultra Pressure Liquid Chromatography) coupled to a Quattro Premier XE mass spectrometer and on a Waters HPLC coupled to a LCT mass spectrometer in order to determine the exact mass of EBI2 ligand. Due, probably, to low amounts of the entity, no overall clear result was obtained.

5.6 Purification of EBI2 $L_2$ and from Human Septic Liver

In order to concentrate and isolate EBI2 ligand from human pathological liver tissue, we tested 8 livers from human sepsis. 2 livers out of 8 displayed significant activation of EBI2.

We extracted 1.8 kg human septic liver using the following procedure: Liver tissue was homogenized within 7 volumes of a mixture of methanol-water-acetic acid (90:9:1). After 30 min centrifugation (10,000 g, 4° C.), supernatant was filtered on Whatman paper. Filtrate was then diluted 3 times with water+0.1% TFA. Extract was loaded on a Delta Pak C18 column (400×40 mm) and the column was washed with 20% MeCN+0.1% TFA. Elution was performed with 80% MeCN+ 0.1% TFA, 100 mL/min. Then we performed several HPLC fractionation of this extract in order to purify the biological entity responsible for EBI2 activation (see FIG. 7).

5.7 Specific Activation of hEBI2 with a Sheep Septic Liver Extract

In order to overcome the limitation of human tissue availability, we investigated several sepsis animal models as potential source of 'active' material. We detected specific activation of EBI2 with a liver extract from a peritonitis sheep sepsis model (FIG. 8). Sheep liver from peritonitis sepsis model was thus considered as an additional source of material for the purification of EBI2 ligand.

5.8 Purification of EBI2 Ligand from Sheep Sepsis Liver

Since identification of EBI2 ligand purified from human sepsis liver tissue was unsuccessful (mainly explained by low recovery of active material), we initiated purification of EBI2 ligand from sheep sepsis liver, since we previously confirmed specific activation of hEBI2 receptor with liver extract originated from a sheep sepsis model.

Extraction and Purification Procedures

Two kilograms of sheep liver were extracted and fractionated following 6 steps of liquid chromatography. We obtained pure fractions which potently activated hEBI2 receptor (FIGS. 9A-F).

Liver tissue was homogenized within 7 volumes of a mixture of methanol-water-acetic acid (90:9:1). After a 30 min centrifugation (10,000 g, 4° C.), the supernatant was filtered on Whatman paper. Filtrate was then diluted 3 times with water+0.1% TFA.

The extract was loaded on a Delta Pak C18 column (400× 40 mm) and the column washed with 20% MeCN+0.1% TFA. Elution was performed with 80% MeCN+0.1% TFA, 100 mL/min.

$1^{st}$ HPLC Separation:

Column: 19×150 mm C18-300 Symmetry, 5 g Waters; 19 mL/min Gradient from 50 to 65% MeCN+0.1% TFA.

$2^{nd}$ HPLC Separation Column:

7.75×250 mm C8-300, 5µ, ACE, 3 mL/min Active fraction from the first LC separation is diluted 2 times with 0.1% TFA and loaded on the column. Elution gradient: 40 to 46% MeCN+0.1% TFA at 0.2%/min.

$3^{rd}$ HPLC Separation Column:

7.75×250 mm C18-300, 5µ, ACE, 2.8 mL/min Active fractions from the second LC separation were diluted 3 times with 0.1% HCOOH and loaded on the column. Elution gradient: 35 to 65% MeCN+0.1% HCOOH at 1%/min.

$4^{th}$ HPLC Separation Column:

4.6×150 mm HSF5, 3µ, Supelco, 0.8 mL/min Active fraction from the third LC separation were diluted 3 times with water and loaded on the column. Elution was at 41% MeCN.

$5^{th}$ HPLC Separation Column:

4.6×150 mm Symmetry-300, 3.5µ, Waters, 1.3 mL/min Active fractions from the 4th LC separation were diluted 3 times with water and loaded on the column. Elution was at 41% MeCN.

6th HPLC Separation Column:
4.6×150 mm Diphenyl, 5µ, Vydac, 1.5 mL/min Active fractions from the 5th LC separation were diluted 2 times with 0.1% Ammonium acetate 10 mM, and loaded on the column. Elution gradient: 26 to 31% MeCN-ammonium acetate 10 mM (9:1) at 0.1%/min.

5.9 Identification of EBI2 Ligand(s) in Sheep Septic Liver Extract

Identification of EBI2 Ligand: MS Analysis.

1—A first set of MS analyses of the active samples (step 5) did not succeed in revealing a candidate mass for the EBI2 ligand, probably because of low amounts of pure molecule. Several contaminants were present in the samples, hindering identification of specific signals. In addition, no clear differences could be detected between active and control samples 2—An additional HPLC purification step of the samples from step 5 was performed (step 6). Prior to MS analysis, the samples were concentrated and cleaned using C18 Zip-Tips. The final elution was with 80% ACN+10 mM ammonium acetate. The eluted samples were injected directly to an Orbitrap MS (Thermo) equipped with a NanoMate (Advion) device. MS analysis of the active fractions showed four peaks with significant intensities in both step 5 (Active 1) and step 6 (Active 2), which were negligible in control samples. Ions with masses m/z 383.3303, 401.3408, 441.3332 were observed in positive ion mode, while m/z 477.3582 was observed in negative ion mode (FIG. 10).

Hypothesis:

Positive Mode:

441.3332=>$[C_{27}H_{46}O_3Na_1]^+$ (mass accuracy in ppm: −1.5)

401.3408=>$[C_{27}H_{45}O_2]^+$ (−1.5 ppm)

383.3303=>$[C_{27}H_{43}O_1]^+$ (−1.5 ppm)

Negative Mode:

477.3582 $[C_{29}H_{50}O_5]^+$ (+1.5 ppm)

Four elemental compositions were obtained with good mass accuracy from four common ion signals detected in both active fractions. The ion corresponding to mass m/z 441.3332 could be assigned to the sodium adduct of the molecule $C_{27}H_{46}O_3$ (M), while mass m/z 477.3582 to the acetate ($CH_3COO^-$ or $OAc$) adduct of M. Furthermore, the ions with masses 401.3408 and 383.3303 could be assigned to a single and double loss of water, respectively, from the protonated molecular ion. The resulting hypothesis is therefore that the compound M=$C_{27}H_{46}O_3$ with a theoretical mass that of 418.3447 was detected as: $[M+Na]^+$, $[M+H-H_2O]^+$ and $[M+H-2H_2O]^+$ in positive ion mode, and $[M+OAc]^-$ in negative ion mode. Neither protonated $[M+H]^+$ nor deprotonated $[M-H]^-$ ions were detected.

In addition, MS/MS experiments were performed with the active fractions on the four masses. No fragments were obtained from m/z 441.3332 and 477.3582, giving credit to the hypothesis that these correspond to the sodium and acetate adducts, respectively. This is because the gas-phase collision induced dissociation leads predominantly the detachment of sodium or acetate ion instead of fragmenting the molecule. Both $Na^+$ and $OAc^-$ ions could not be detected due to "low mass cutoff" (instrument specific) in the MS/MS experiments. Few fragments were obtained by MS/MS of m/z 383.3303. Among them, one water loss at m/z 365.3205 (0.7 ppm) was detected. No further structure assignment was attempted on the fragments of m/z 383.3303. No MS/MS was performed on m/z 401.3408 due to its low intensity.

Database query of mass 418.3447 provided mainly oxidized cholesterol (oxysterols) or vitamin D derivatives. From database analysis the following ligand candidates were identified:

39 Cholesterol Derivatives Consisting of:

8 keto-diols 27 triols 2 acids 1 diol+epoxy 1 diol+aldehyde

Compounds Tested for EBI2 Activation in Aequorin Assay 1 (25R)-5-alpha-spirostan 2 5-alpha-cholestane-3,6-dione 3 5-alpha-cholestane-2,3-dione 4 5-alpha-cholestan-3,7-dione 5 cholesta-4,6-dien-3-one 6 3-beta-hydroxycholest-4-en-6-one 7 5-alpha-hydroxy-6-keto cholesterol 8 cholesta-3,5-dien-7-one 9 5-Cholesten-3b-ol-7-one 10 4,5-epoxy-3-cholestanone 11 4-beta,5-epoxy-5-beta-cholestan-3-one 12 Cholesterol 13 b-sitosterol 14 25-hydroxycholesterol 15 22(S)-hydroxycholesterol 16 22(R)-hydroxycholesterol 17 1-alpha,25-Dihydroxyvitamin D3

18 24(R),25-Dihydroxyvitamin D3

19 25-Hydroxyvitamin D3

A list of candidate molecules with $C_{27}H_{46}O_3$ molecular formula was prioritized, and tested for hEBI2 activation. Such prioritization list was established from cholesterol derivatives identified as intermediates in the cholesterol metabolism pathway and from known vitamin D derivatives. This list contained 12 cholesterol derivatives and 5 vitamin D derivatives with $C_{27}H_{46}O_3$ molecular formula (mass 418.3447)

3 oxysterol and 3 vitamin D3 compounds were tested for EBI2 activation in an aequorin assay.

Among these candidate molecules two related oxysterols, cholest-5-ene-3b, 7b, 25-triol (7b,25DHC), depicted by the compound of Structure I and cholest-5ene-3b, 7b-diol (7bHC), depicted by the compound of Structure II induced specific activation of EBI2 receptor with EC50 values close to 50 nM and 15 µM respectively, while cholest-5-ene-7-methoxy,3b-ol, depicted by the compound of Structure III did not activate EBI2 (FIG. 11), underscoring the relevance of the alcohol groups and their position in structure-activity relationship.

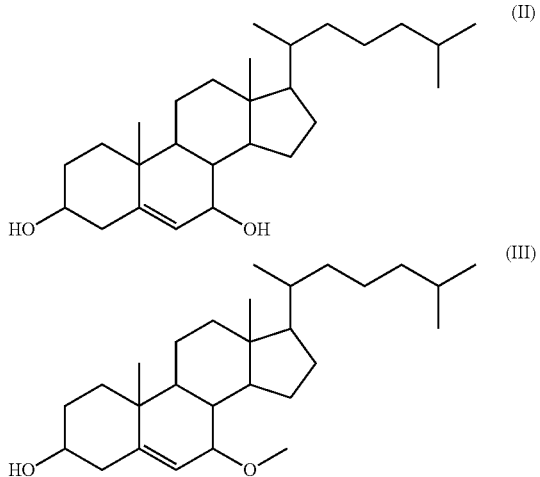

(II)

(III)

5.10 Confirmation of Specific EBI2 Activation with Cholesterol Derived Ligand in CHO and HEK Cells.

We demonstrated that cholest-5-ene-3b,7b, 25-triol (7b, 25DHC) specifically and selectively activates hEBI2 compared to WT CHO-AeqGqi5 cells and unrelated GPCRs such as orphans HCR and GPR23 (FIGS. 12 and 14). We also confirmed activation of hEBI2 by 7b,25DHC in different CHO-Aeq cell backgrounds (Gqi5 and Gα16 (=WTA11)) (FIG. 14). In addition we demonstrated activation of mouse EBI2 receptor with 7b,25DHC (FIGS. 13 and 14). Finally, we confirmed activation of hEBI2 by 7b,25DHC with hEBi2-HEK-Aeq Gα16 cells (pCAeqG9) and hEBi2 transiently transfected in HEK T cells (data not shown).

5.11 MS of 7,25-OHC Standard Compounds

Synthesized standard samples 7a25-OHC and 7b25-OHC were analysed with the same MS methods as described in 5.9. At relatively low concentration, only $[M+Na]^+$ m/z 441.3338 (0.3 ppm), $[M+H-H2O]^+$ m/z 401.34140 (0.5 ppm) and $[M+H-2H2O]^+$ m/z 383.33084 (0.01 ppm) were detected in positive ion mode, and $[M+OAc]^-$ m/z 477.3585 (0.2 ppm) in negative ion mode in the presence of ammonium acetate. No protonated and deprotonated signals were detected. These observations are consistent with those obtained from the active fractions.

5.12 Conclusion

We purified EBI2 natural ligand from sheep liver obtained from a peritonitis sepsis model. Although EBI2 activation was initially detected in a human septic liver extract, human pathological material was difficult to obtain and purification of EBI2 ligand from 1.8 kg of human septic liver did not enable us to isolate sufficient amounts of active entity to be detected by MS analysis.

Mass spectrometry analysis on purified sheep liver active fractions, resulted in the identification of a candidate mass 418.3447 and an associated molecular formula $C_{27}H46O3$. Compounds displaying such features are corresponding essentially to cholesterol or vitamin D derivatives.

Following candidate selection and screening for hEBI2 activation (aequorin assay), we identified cholest-5-ene-3b, 7b,25-triol (7,25-dihydroxycholesterol) ("7b,25DHC") and cholest-5-ene-3b,7b-diol (7-hydroxycholesterol) ("7bHC") as two active ligands at hEBI2. Cholest-5-ene-3b,7b, 25-triol potently activated hEBI2 with EC50 value around 50 nM and displayed an efficacy greater than 100% compared to the ATP response (endogenous P2Y receptors).

Specificity and selectivity of cholest-5-ene-3b,7b, 25-triol for hEBI2 was demonstrated compared to WT CHO-Aeq cells and unrelated GPCRs.

Activation of hEBI2 with cholest-5-ene-3b,7b, 25-triol was demonstrated in CHO-K1 cells and HEK293 cells.

5.13 Pharmacological Profile of Oxysterols at the EBI2 Receptor

Once we demonstrated activity for 7b,25DHC and 7bHC at the EBI2 receptor we set out to determine which is the most likely active compound in vivo. 7b,25DHC is not a compound naturally produced by an enzymatic reaction, but rather is a product of auto-oxidation under specific conditions. We conducted, therefore, a pharmacological characterization of the oxysterols/EBI2 interaction.

Methodology
Compounds:

7a,25DHC(CAS No. 64907-22-8) and 7b,25DHC (CAS No. 64907-21-7) were synthesized from the 7-keto precursor as described below. 7a,27DHC (CAS No. 144300-24-3), 7b,27DHC (CAS No. 240129-43-5) were purchased from Avanti Polar Lipids Inc. (Alabaster, A L, USA). 7aHC (CAS No. 566-26-7) was batch synthesized in house. 7bHC (CAS No. 566-27-8), 25HC (CAS No. 2140-46-7), and cholesterol (CAS No. 57-88-5) were purchased from Sigma-Aldrich (Buchs, Switzerland).

Compound Preparation

If not stated otherwise compounds were dissolved at 10 mM in DMSO or ethanol (cholesterol, 25MDC). Serial dilutions were carried out in 90% DMSO (FLIPR, GTPgS) or assay buffer (binding assay). For cell based assays final DMSO concentrations is kept below 1%. In order to prevent adsorption of hydrophobic compounds to the assay plates 0.1% (2-hydroxypropyl)-βcyclodextrin (Aldrich, #33259-3) is added.

Cell Line

If not stated otherwise, the same Chinese hamster ovary (CHO) cell line called E2 which was used for the ligand identification was used in these experiments. This cell line is expressing (1) the recombinant human EBI2 receptor, (2) the promiscuous Gqi5 protein as well as (3) apo-aequorin.

FLIPR

Cells were seeded in black/clear bottom, poly-D-Lysine coated 384-well plates at a cell density of 10,000 cells/25 µL/well, using culture medium. Cells were cultured for 24 hours at 37° C./5% $CO_2$. Culture medium was removed and for cell loading, 20 µl per well of loading buffer (Calcium-4 no wash dye) were distributed into the wells and the plates were incubated for 60 min at 37° C. in 5% $CO_2$. With the FLIPR pipettor, 10 µl of the different compounds were added to the cells and the subsequent fluorescent changes monitored for 3 minutes. Using the FLIPR software tool, 2 values of fluorescence calcium responses were exported: Fmax, the fluorescence at the peak and Fbasal corresponding to the value prior to compound injection. From these two values, the calcium response is normalized with respect to the calcium baseline values using dF/F=(Fmax−Fbasal)/Fbasal. The maximum dF/F is called Emax.

Membranes Preparation

CHO cells stably expressing human EBI2 (E2) were grown in roller bottles (Corning #431191) to confluency, washed with phosphate buffered saline (PBS) once and frozen at −80° C. The frozen cell pellets were resuspended in ice-cold homogenization buffer (10 ml/gram, 20 mM Tris pH7.2) supplemented with a protease inhibitor cocktail (Complete™, Roche, #05 056 489 001-14302200). The cell suspension was then homogenized using a Dounce homogenizer (10 strokes) with a driller. After centrifugation at 110000×g for 45 minutes and removal of the supernatant, pellets were resuspended in sucrose buffer (50 mM Tris pH7.2, 250 mM sucrose, 10% glycerol) by vortexing. The suspension was again homogenize using a Dounce homogenizer (10 strokes) and spun at 100000×g for 45 minutes. The supernatant was discarded, the pellet resuspended in sucrose buffer, protein concentration determined, aliquoted and frozen at −80° C. These membrane preparations were used in binding as well as GTPgS assays.

GTPγS Assay

Reaction were carried out in 96 well plates (OptiPlates™, Perkin Elmer #6005299). Ten micrograms of EBI2 membranes are dissolved in 40 µl of buffer A (20 mM Hepes pH 7.4, 100 mM NaCl, 1.5 mM $MgCl_2$, Saponin 10 µg/ml) supplemented with 10 µM GDP. After addition of 20 µA scintillation proximity assay (SPA) beads (100 µg/well, Amersham, RPNQ0001) components are gently mixed and incubated at RT for 15 minutes. Twenty microliters of compound diluted in buffer A and 20 µl of $GTP\gamma^{35}S$ (Perkin Elmer NEG030X) is added before incubation for one hour at RT. Plates are transferred and counted in a TopCount (Perkin Elmer NXT HTS™) and counts are analysed plotted and to determine half maximal concentrations of activation using standard software (Prism™, GraphPad Software Inc.).

Binding Assay

Materials

Lyophilized wheat germ agglutinin scintillation proximity assay (SPA) beads (RPNQ0001) were purchased from GE Healthcare (Buckinghamshire, UK). One vial (500 mg) is reconstituted by adding 5 mL of distilled water to give a final concentration of 100 mg/mL. Reconstituted SPA beads must be stored at 4° C., but must not be frozen. [3H]-7a,25-OHC, was synthesized by reduction of the 7-keto, 25DHC in the presence of 3H-L-selectride. This protocol yields equal amounts of 7a,25DHC and 7b,25-OHC (see below). [3H]-7a, 25DHC used in this experiment was Batch RSE 436-2 with a specific activity of 1024 GBq/mmol) and stored at −20° C. EBI2384-well plates (Cat. No. 6007290, white polystyrene, flat square bottom) were purchased from Perkin Elmer (Boston, USA).

Synthesis of Radiolabeled 7,25DHC

On a tritiation line, an evacuated, two-necked flask (V=2 mL) was set under $^3H_2$ (99% $^3H_2$, 179.25 mmol, p=728 mbar) at 296K, Subsequently, butyl-lithium in hexane (160 µmol, 100 µL, c=1.6M) and tetramethylethylenediamine (200 µmol, 30 µL) was added. After 55', the suspension was cooled with liquid $N_2$, the excess of $^3H_2$ was taken back to the waste reservoir and the solvent was evaporated. Then, the residue was set under $N_2$, THF (5004) was added, the suspension was diluted with sec-butyl-borane in THF (160 µmol, 160 µL, c=1M) and cooled to −90° C. At this temperature, a solution of 1 (24 µmol, 10 mg) in THF (500 µL) was added within 1' and the reaction mixture was stirred for 90', while the temperature was raised slowly form −80° C. to −50° C. After this time, acetone (1504) was added and the reaction mixture was stirred for further 90', while the temperature was raised slowly form −50° C. to −8° C. At the end, the reaction mixture was quenched with 1.0N NaOH (250 µL) and 30% $H_2O_2$ (250 µL) and stirred for 15' at room temperature.

Subsequently, the reaction mixture was frozen in liquid nitrogen, evaporated to dryness and co-evaporated with ethanol (4×1 mL). The residue was filtered over a pad of $SiO_2$ (1 g) and the product was eluted with $CH_2Cl_2$/MeOH 95:5 in order to yield 851 MBq of a mixture of 2 and 3 (dissolved in 14 mL ethanol; α-isomer/β-isomer=58:42), which was separated by preparative reversed phase HPLC on MN Nucleodur Sphinx RP (5 µm, 8×150 mm, T=20° C., λ=210 nm; eluent A: water+0.1% TFA; eluent B: CH3CN+0.1% TFA). Thus, two enriched fractions of 2 (59.94 MBq, α-isomer/β-isomer=70:30) and 3 (108.04 MBq, α-isomer/β-isomer=38:62) were obtained, each after extraction on solid support StrataX (2×100 mg). The enriched, pre-purified fractions were further purified by preparative reversed phase HPLC on Water's SunFire C18 (5 µm, 10×250 mm, T=40° C., λ=210 nm; eluent A: $H_2O$/MeOH=95:5; eluent B: $H_2O$/MeOH=5:95) in order to yield 50.6 MBq of diastereomerically pure 2 (α-isomer/β-isomer=99.9:0.1) and 51.4 MBq of diastereomerically pure 3 (α-isomer/β-isomer=0.1:99.9).

$K_D$ Determination

The $K_D$ determination was performed using a fixed concentration of membranes and beads (respectively 20 µg and 200 µg per well) and a range of [$^3H$]-BYX998 concentrations from 0.05 to 300 nM. These solutions were made in buffer containing 50 mM Tris; 100 mM NaCl; 5 mM $MgCl_2$ and 0.1% Cyclodextrine.

The specific binding was measured in presence of a constant 7a,25DHC (NVP-BYX998-NX-4) concentration of 10 uM final and the corresponding total binding was measured with buffer instead of NVP-BYX998-NX-4.

IC50 Determination

The SPA assay was performed in a final volume of 50 µl per well in a 384-well polystyrene Opti plate. The components were added into the wells as follows:

10 µl tested compounds in 50 mM Tris; 100 mM NaCl; 5 mM $MgCl_2$ and 0.1% Cyclodextrine.

Total binding was determined by the addition of 10 µl of 50 mM Tris; 100 mM NaCl; 5 mM $MgCl_2$ and 0.1% Cyclodextrine and non-specific binding was determined by the addition of 10 µl NVP-BYX998-NX-4 (final concentration of 10 µM).

20 µL of 10 nM final [3H]-BYX998 in assay buffer (50 mM Tris-HCl, 100 mM NaCl, 5 mM $MgCl_2$ and 0.1% Cyclodextrine).

20 µL of a mixed bead and membrane suspension in assay buffer, in order to get a final concentration of 20 µg membranes/well and 200 µg beads/well.

The plates were sealed and shaken at room temperature for 10 minutes then allowed to stand at room temperature for at least 12 hours. The plates were counted using a Perkin Elmer TopCount reader, each well being counted for 1 minute.

Each IC50 determination was performed with 11 concentrations.

A standard data reduction algorithm was used to calculate the percentage of specific binding in the presence of test compound as follows:

$$((B-NSB)/(Total-NSB)) \cdot 100, \text{ where}$$

B=Binding in the presence of test compound (in cpm)
NSB=Non-specific binding in the presence of excess inhibitor (in cpm)
Total=Binding in the absence of test compound (in cpm)
Curve fitting of the normalized concentration response curves using a four parameter logistic fit is then performed using XLfit (v.2 or v.4, IDBS, Guildford, UK). The equation used is XLfit equation no. 205 for a one site sigmoidal dose response curve: $Y=A+((B-A)/(1+((C/X)^\wedge D)))$, where A=min, B=max, C=IC50, D=slope. By default, min is fixed at 0, whereas max is not fixed.

Ki is calculated according to the Cheng-Prusoff equation (Cheng, Y. and Prusoff, W. H. (1973). Relationship between the inhibition constant (K1) and the concentration of inhibitor which causes 50 percent inhibition (I50) of an enzymatic reaction. Biochem. Pharmacol. 22, 3099-3108):

Aequorin Assay

Using the aquorin assay we found out that 7a,25DHC activated EBI2 stably expressed in CHO cells with a EC50 of 18.4 nM compared to the less potent 7b,25DHC for which an EC50 of 398 nM was measured (FIG. 15).

Methodology

Stable cell line expressing human EBI2 (in pcDNA3.1 vector) and Gα16 was generated with parental CHO cells that stably express apo-aequorin (Euroscreen CHO-A12 cell line). The cells were seeded into 384 well black clear bottom plates (Greiner Bio-one) at 10,000 cells/25 µl well in F12 medium containing 3% FBS and incubated overnight. Coelenterazine (20 µM final) was added into the cell plates at 25 µl/well. The cell plates were returned to incubator for 3 hrs. The compounds were diluted 1:20 into an intermediate plate with Tyrode buffer (130 mM NaCl, 2 mM CaCl2, 5 mM NaHCO3, 5 mM KCl, 1 mM MgCl$_2$, 20 mM HEPES, pH 7.4). 12.5 µl/well of pre-diluted compounds were transfered into the cell assay plate and read on LumiLux™ (Perkin Elmer) for flash luminescence.

An algorithm similar to area under curve (AUC) was created in house to analyze the aequorin kinetic data, which was named Slope Threshold (Slope 100). The algorithm defines the beginning and the end of the luminescence intensity peak by comparing the difference in intensity of each time point with an earlier time point, and determining if the difference exceeds a defined threshold, which was usually set at 100. If it does, then the intensity of the later time point is added into the Slope Threshold's sum.

cAMP Assay

Similarly, in the cAMP assay, the stereoisomer 7a,25DHC (EC50=10.3 nM) shows to be more potent than the stereoisomer 7b,25DHC (EC50=10.6 µM) (FIG. 16).

Methodology

The same stable EBI2 cell line used in the aequorin assay was used in cAMP assay. 10,000 cells (25 µA) were seeded per well into white solid 384-well plate and incubated in 37° C. incubator overnight. 500 nl of compound was then transferred into each assay well, followed by 5 µl of forskolin addition for a final concentration of 30 µM. Cells were returned to a 37° C. incubator for 30 min. Finally 15 µl each of HiRange D2-cAMP and anti-cAMP cryptate were dispensed per well. After >1 hr room temperature incubation, data acquisition was done in the time-resolved FRET (fluorescence-resonance energy transfer) mode on Envision™ or ViewLux™ (Perkin Elmer). The ratio between the acceptor fluorescence signal (A665 nm) and donor fluorescence signal (A620 nm)×104, representing the FRET between the conjugated cAMP and the anti-cAMP antibody, was calculated and plotted on Y-axis. The higher the signal, the lower endogenous cAMP concentration is in the sample.

Beta-Arrestin Interaction of EBI2 after Activation with Oxysterols (DiscoveRx)

It has been shown for a large number of GPCRs that activation of the receptor leads to phosphorylation of residues at the C-terminus and recruitment of β-arrestin.

Subsequently, the GPCR/β-arrestin complex is incoparated into clathrin-coated pits which leads to the internalization of receptor containing vesicles and desensitization of the receptor signaling.

Several assay technologies (Transfluor™, (Ghosh, R. N., et al. (2005). Quantitative cell-based high-content screening for vasopressin receptor agonists using transfluor technology. J Biomol Screen 10.; Granas, C., at al. (2005). High content screening for G protein-coupled receptors using cell-based protein translocation assays. Comb Chem High Throughput Screen 8.); Pathhunter™, (Hammer, M. M., et al. (2007). A novel enzyme complementation-based assay for monitoring G-protein-coupled receptor internalization. Faseb J, 21; Wehrman, T. S., at al. (2005). Enzymatic detection of protein translocation. Nat Methods 2), Tango™, (Barnea, G., et al. (2008). Here we have applied the Pathhunter™ technology (DiscoverRx) to probe for an interaction of EBI2 with B-arrestin. For that human EBI2 was cloned into the Prolink™ vector (DiscoveRx) for GPCR-prolink fusion protein production. Parental HEK293 cells that stably express β-arrestin2-β-gal-EA fusion protein (HEK293-BAEA) were detached and transiently transfected with hEBI2-prolink vector using Fugene6 transfection reagent in suspension mode. Transfected cells in assay medium (Phenol Red-free DMEM with 10% FBS) were plated into white solid 384 well plates at 15,000 cells/25 µl/well. After overnight incubation, 200 nl of test molecules were transferred into the cell plates by Pin-Tool™ (GNF Systems) followed by 1-2 hour incubation at 37° C., 5% CO2. Flash detection reagents were added at 12.5 µl/well. After 5 min—1 hr room temperature incubation, the cell plates were read on CLIPR™ (Perkin Elmer) or Acquest™ (Molecular Devices) for luminescence signal. The results shows that 7a,25DHC (compound of formula IV) and 7b,25DHC (compound of formula V) activate hEBI2 with EC50 of 8.0 nM and 837 nM (48% efficacy), respectively (FIG. 17).

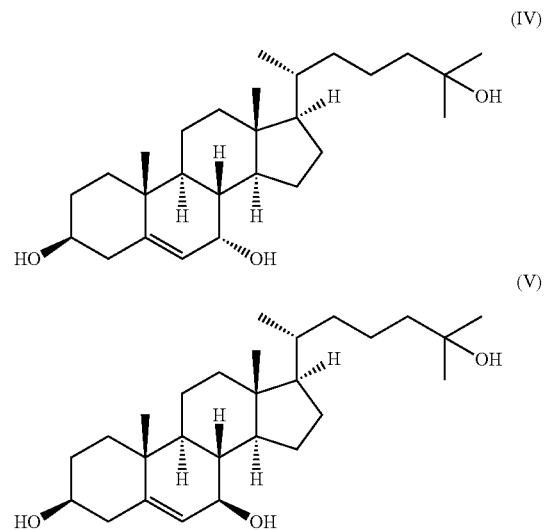

5.14 7a,25-OHC is the Oxysterol which was Purified from Tissue Extracts 7a,25DHC which was synthesized by modification of a known method (method of synthesis 1) (Li, D. & Spencer T. A. (2000) Synthesis of 7a-hydroxy derivatives of regulatory oxysterol, Steroids 65, 529-535) or according to the one-step process (method of synthesis 2) as shown below.

Method of Synthesis 1

From commercially available 5-cholesten-3b,25-diol (Steraloids, C6510-000), the diols are protected with benzoyl chloride, followed by C7 oxidation with pyridinium chlorochromate in absolute benzene and molecular sieve under microwave irradiation at 150° C. for 4 h. L-selectride in THF at −78° C. facilitated diastereo-selective reduction (20:1) of C7 carbonyl to 7a-hydroxy group. The two diastereomers can be conveniently isolated using silica gel column chromatography (75% ethyl acetate in hexnanes to 100% ethyl acetate).

Deprotection of di-benzoyl ester yielded the final product 7a,25DHC in overall 14% yield (4 steps).

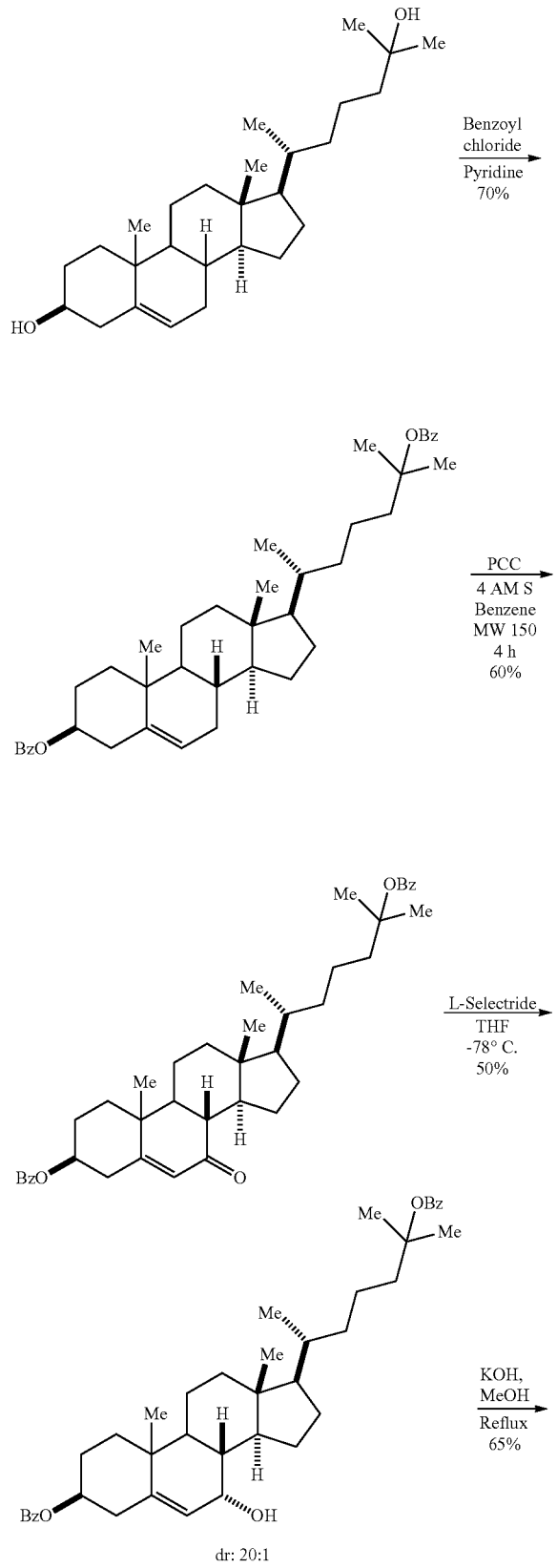

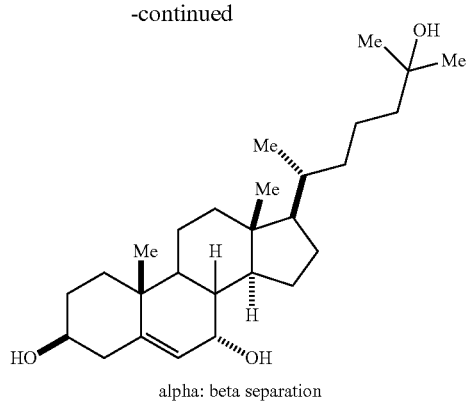

alpha: beta separation

Method of Synthesis 2

From commercially available 5-cholesten-3β,25-diol-7-one (Steraloids, C6510-000), the C7-carbonyl group was diastereoselectively reduced (dr~20:1) with L-Selectride in THF at −78° C. for 5 h, after work-up and column chromatography, the pure 7a,25DHC can be obtained in one step at around 50% yield. This one step process is very useful for synthesizing radiolabelled (e.g. $^3$H-labeled) 7a,25DHC.

As shown in Table 3 above, compound 7a,25DHC proofed to be more potent than 7b,25DHC.

In order to determine the exact nature of the oxysterol we purified from sheep liver we developed an analytical method to separate the two different oxysterols stereoisomers (7a, 25DHC versus 7b,25DHC) by liquid chromatography.

Methodology

In order to determine the 7,25DHC stereochemistry of bioactive material from the tissue extracts we first established an analytical method to separate the two diastereomers 7a,25DHC and 7b,25DHC using reference compounds. In a second step retention time for the reference compounds were compared to bioactive material from the tissue extracts. The samples used in this experiment were from two sheep liver preparations, S5 and S9, and three biologically active fractions for each preparation were collected in the last step of purification.

The 7a,25DHC and 7b,25DHC were separated by liquid chromatography (LC) on a Thermo-Fischer Hypersil Gold™ column. Water (5 mM NH$_4$Ac) and acetonitrile (0.1% acetic acid) were used a mobile phases. The gradient ranged from 20% to 85% acetonitrile over 12 min (FIG. 18A). The compounds were selectively detected by electrospray mass spectrometry, in 2 instruments. In both cases, the in-source fragmentation product (loss of $2H_2OC_{27}H_{47}O_3^+ \rightarrow C_{27}H_{43}O^+$, 383.3308 Da) was monitored, as well as 2 CID (collision induced decay) fragments of that specific ion at 253.27 and 157.18 Da. Only if all 3 ions are simultaneously observed is it concluded that DHC is detected.

First a Thermo Finnigan LTQ™ instrument was used. It is capable of fast data acquisition, allowing full use of the liquid chromatography retention time (RT) peak separation. In all six samples only 7a,25DHC and no 7b,25DHC was detected (FIG. 18B). We confirmed these results on a second instrument (Thermo LTQ-Orbitrap™) which displays a higher mass resolution and accuracy but a slightly reduced liquid chromatography resolution.

5.15 Isolation of Natural EBI2 μLigand from Pig Liver

Parallely to the broad pharmacological characterization of the oxysterols capable of modulating EBI2, the purification of natural EBI2 ligands from pig liver extracts has been attempted.

Extraction Protocol

10 Kg of pig liver, was grinded in a meat grinder, and were homogenized with (every 500 g of wet grinded tissue with 500 mL water) using vita mix, and extracted with 20 L of 1:1 hexanes and isopropanol mixture for 1 h. Pellets and two layers of liquid were separated by 30 min centrifugation (15000 g, 4° C.), organic layers were collected, dried over sodium sulfate, and concentrated to give pale whitish solid (~1 kg, not totally dry).

Fractionation Protocol

Fractionation step 1:1 kg of crude extract was loaded onto 10 kg silica gel manual column chromatography and eluted sequentially with 2 column volumes (16 L) of 100% hexanes, 10%, 25%, 50% and 75% EtOAc in hexeanes, 100% EtOAc, and 10% EtOAc in MeOH, and total 40 fractions were collected (4 L/fraction). The fractions were dried down by rotary evaporator at reduced pressure and 25° C. and activity was tested by DiscoverX beta arrestin assay.

Fractionation step 2: Normal Phase-HPLC, 21×250 silica gel column, elution conditions: 100% hexanes for 5 min, 100% hexanes to 100% EtOAc for 60 min, 100% EtOAc for 10 min, 0-20% Methanol in EtOAc for 20 min, with 1 gram loading per column, 18 duplicate runs)

Fractionation step 3: Normal Phase-HPLC, 4.6×250 silica gel column, F3 are EBI2 specific from step 2 refractionation and are pooled from 18 parallel runs and subjected into step 3 normal phase HPLC with dichloromethane (DCM) and Methanol as the solvent, 5% DCM for 5 min, 5-50% DCM in Methanol for 60 min, hold at 50% DCM for 20 min)

Fractionation step 4-Reverse phase C18 (4.6×250) HPLC column chromatography, 4.6×250 C18 resin, elution conditions: 50-100% acetonitrile (ACN) in H$_2$O without TFA modifier, 1 mL/min/fractionation)

Fractionation Step 5-Reverse phase C4 (2.0×250) HPLC column chromatography, 0.35 mL/min/fraction, eluted from 50%-100% ACN/H$_2$O, for 2 h)

LC-MS analysis of active and inactive fractions was done in Agilent 1200 series using reverse phase HPLC with C4 column (2.0×50 mm, YMC™ Pro C4, S-5, 120 A). MS acquisition parameters: Instrument: Agilent 6520 Accurate-Mass Q-TOF LC/MS Gas Temperature: 350° C. Drying Gas: 10 l/min Nebulizer: 45 psig VCap: 4000 V Capillary: 0.047 μA Chamber: 0.63 μA Fragmentor: 175 V Skimmer: 65 V OCT 1 RF Vpp: 750 V Acquisition mass range: 50-1500 Acquisiton rate: 1 spectra/s Reference mass: 121.050873 and 922.009798 (reference solution was infused during the entire run time).

Samples were eluted at 0.35 mL/min with a gradient from 30 to 100% acetonitrile in H$_2$O with 0.1% formic acid as the modifier. The column was kept at 30° C.

A pure fraction with a major peak at 9.77 min in total ion chromatogram (positive mode) was identified. Ions with masses m/z 365.3202, 383.3311, 401.3411 and 441.333 were observed in positive ion mode, rationalized as M+H–3H$_2$O, M+H–2H$_2$O, M+H–H$_2$O, and M+Na. The M+H not observed at 419.3. These data further confirm and support the findings shown above in section 5.9.

Synthesized 7a,25DHC and 7b,25DHC were compared with the active fractions obtained by fractionation of the pig liver extracts as described above. The synthesized compounds and the active fractions were analysed for retention time in liquid chromatography and MS/MS (FIG. 19). These results indicate that the natural ligand of EBI2 isolated from pig liver extracts is 7a,25DHC.

$^1$H-NMR of 7a,25DHC (FIG. 20A) and 7a,25DHC isolated EBI2 natural ligand (FIG. 20B) from pig liver were analysed by NMR. Scale-up extraction/fractionation of pig liver (35 Kg scale) following fractionation as described above yielded about 100 micrograms of substantially pure EBI2 ligand. $^1$H-NMR analysis further confirmed that the natural EBI2 ligand purified from pig liver is 7a,25DHC.

5.16 Results

We identified that other than the hydroxylation at the 3 position, hydroxylation at the 7 and at the 25 position is necessary for potent activation of EBI2. At the 7 position the axial alpha position is much preferred over the equatorial beta position (compound 7a,25DHC as depicted in Formula IV and compound 7b,25DHC as depicted in Formula V). Hydroxylation of the side chain is preferred at the 25 position although also the 27 compound shows good potency. We find that the rank order potency of different oxysterols in different assays is identical (Table 3)

TABLE 3

Pharmacological characterization of different oxysterols in calcium fluorescence (FLIPR ™), GTPgS and radio-ligand binding assay.

|  | FLIPR (nM) | | GTPgS (nM) | | [$^3$H] 7a,25DHC Binding | |
| --- | --- | --- | --- | --- | --- | --- |
|  | EC50 | SD | EC50 | SD | IC50(nM) | SD |
| 7a,25DHC | 1.9 | 1.8 | 7.5 | 4.0 | 70.4 | 4.4 |
| 7a,27DHC | 4.8 | 3.7 | 5.1 | 1.6 | 362.0 | 32.1 |
| 7b,25DHC | 120.8 | 53.6 | 221.0 | 104.5 | 2632.0 | 110.3 |
| 7b,27DHC | 309.6 | 261.0 | 124.8 | 66.4 | >10000 | |
| 7aHC | 1452.7 | 1162.5 | 497.6 | 266.5 | 3535.7 | 430.5 |
| 7bHC | >10000 | | >10000 | | >10000 | |
| 25DHC | 3031.5 | 2644.7 | 726.7 | 231.8 | >10000 | |
| cholesterol | >10000 | | >10000 | | >10000 | |
|  | n = 3-4 | | n = 3-4 | | n = 3 | |

Using [$^3$H]-7a,25DHC we conducted saturation binding experiments using membranes from CHO cells stably expressing human EBI2. Binding of [$^3$H]-7a,25DHC to EBI2 is saturable with high affinity (Kd=25+/–10 nM (n=3) and displaceable with increasing concentration of 7a,25DHC and other oxysterols. Using the other stereoisomer [$^3$H]-7b, 25DHC we were not able to detect specific binding to EBI2 membranes (data not shown).

5.17 Activation of EBI2 Leads to Phosphorylation in the Map/Erk Pathway

Mitogen-activated protein kinases (MAPK) are serine/threonine-specific protein kinases that respond to extracellular stimuli and regulate various cellular activities.

Methodology

Cells (E2=CHO/AEQ/Gqi5/hEBI2) were seeded at $2 \times 10^5$ cell/well in a 12 well plate (TPP #92012) and incubated at 37° C./5% $CO_2$ overnight. The next day medium was removed and cells were starved in serum-free medium for 4 h. Subsequently compound was added for 5 min at RT before cells were lysed (70 ul, 0.5% Triton-X100, 300 mM NaCl, 50 mM Tris pH7.5, Complete™ protease inhibitor cocktail Roche #04693124001). Cell lysates were resolved by gradient SDS-PAGE (NuPage™4-12%, #NP0322Box), transferred by semi-dry blotting to nitrocellulose (Invitrogen, #LC2001) and probed with a phospho p42/44 MAPK (T202/Y204) rabbit mAb (Cell Signalling #4376S). After treatment with a secondary goat anti rabbit-HRP (Pierce #41460) antibody the blots were developed for chemiluminescence (SuperSignal West Dura™, Pierce #34075) and visualized using a BioRad GEL DOC™ imaging system.

We have tested EBI2 expressing CHO cell line for MAP/ERK phosphorylation and find that 7a,25DHC and other oxysterols according to the invention can potently activate the MAP/ERK signaling pathway by phosphorylating p44/42 MAP kinase (FIG. 21). As a control we have used the parental CHO cell line which does not express human EBI2. Even high 7a,25-OHC concentrations do not activate a MAP/ERK signal in this control cell line.

5.18 Specificity of the Interaction Between 7a,25DHC and 7a,27DHC with EBI2

So far oxysterols have been noted to have various physiological activities namely regulate the expression of genes that participate in both sterol and fat metabolism, serve as substrates for the synthesis of bile acids, and are intermediates in the transfer of sterols from the periphery to the liver (Russell, D. W. (2000). Oxysterol biosynthetic enzymes. Biochim. Biophys. Acta 1529, 126-135). In order to assess potential interactions of the two most potent EBI2 agonists (7a,25-OHC and 7a,27-OHC) we have tested them in a panel of reporter gene assays against the following nuclear hormone receptor: SXR (NR1I2; ENSG00000144852), ERa (NR3A1; ENSG00000091831), FXRa (NR1H4; ENSG00000012504), GR (NR3C1; ENSG00000113580), LXRa (NR1H3; ENSG00000025434), PPARg (NR1C3; ENSG00000132170), RXRa (NR2B1; ENSG00000078380) We find that these two oxysterols did not activate the above-mentioned nuclear hormone receptors at concentrations up to 10 µM. We have also evaluated the same two compounds in a safety panel routinely used for evaluation of compounds during drug development. This included binding assays for 26 different GPCRs, functional assays of 9 different GPCRs, 40 kinase assays, as well as selected ion channels, proteases, transporter and enzyme assays. In none of these assay did we see a significant interaction between either 7a,25DHC or 7a,27DHC and the tested partner (data not shown)

5.19 Oxysterol 7a,25DHC Act as Chemo-Attractants for Immune Cells.

Methodology

Chemotaxis assays were performed in MultiScreen-MIC™96-well plates with 5-µm pore polycarbonate filters (Millipore #MAMIC5S10) Cell suspensions and chemokine dilutions were made in RPMI1640 with Glutamax™ (Invitrogen, #61870-010) supplemented with 1% nonessential amino acids (Invitrogen, #11140-035), sodium pyruvate (Invitrogen, #11360-039), penicillin/streptomycin (Invitrogen, #15140-114), 50 µM β-mercaptoethanol (Invitrogen #31350-010) and 0.5% BSA (Gibco #15260).

B cells (RS11846 or EBV-infected human B-cells) or murine bone marrow-derived dendritic cells were washed once with medium and resuspended at $1 \times 10^6$/ml. 100 µl of this suspension was added into the wells of the filter plate and gently placed into the receiver plate containing 150 µl of a given compound dilution. The final DMSO concentration was less then 0.1%. After migration for 3 hr at 37° C. in an incubator, the filter plate was carefully removed from the receiver plate and discarded. The migrated cells in the receiver plate were resuspended and transferred into round-bottom 96-well plate, centrifuged and resuspended in 100 µl PBS containing 2% FCS and 0.1% $NaN_3$ (FACS buffer). The input cells (100 µl) were similarly processed. For the calculation of the specific migration, a fixed number of beads (10000; Invitrogen #PCB100)) in 20 µl FACS buffer was added and the suspension was analyzed by flow cytometry using a FACS instrument PAS™ (Partec). Cells were identified based on their forward scatter (FSC) and side scatter (SSC) pattern. Chemotaxis is expressed either as total cell number or as percent of input cells.

Figure 20A:
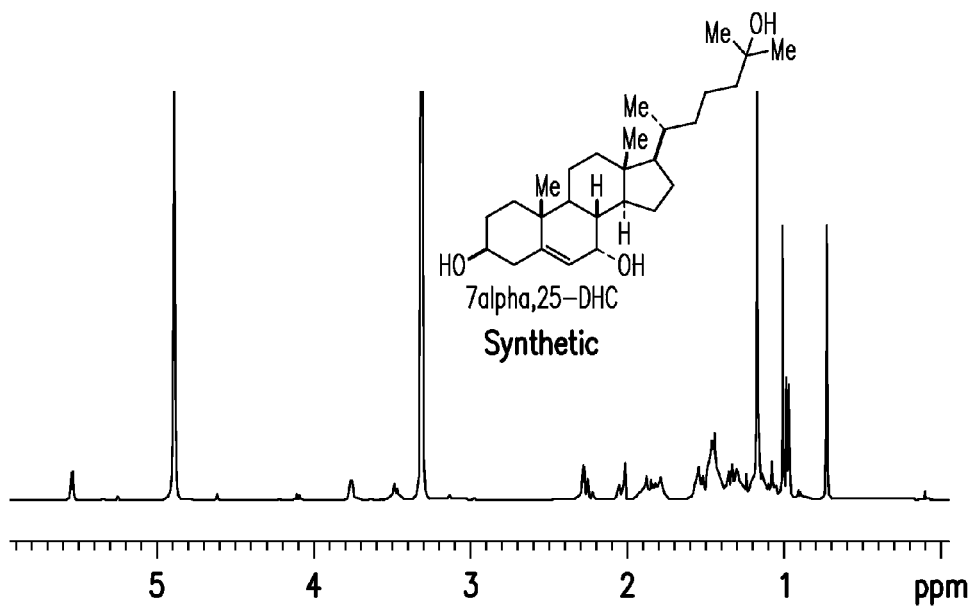
Figure 20B:
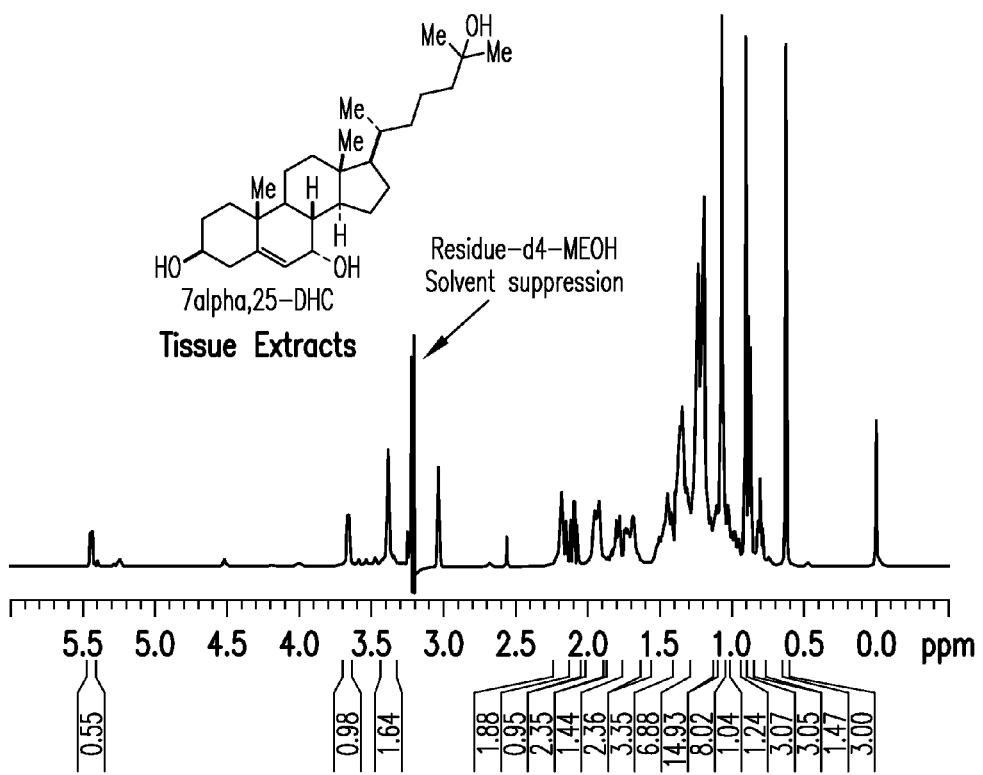

DNA expression arrays from B cells in different stages of their life cycle show a distinct profile of EBI2 expression (FIGS. 22 A and B). While there is clear expression of EBI2 in naïve B cells, B cells from lymph node germinal centers sharply down-regulate EBI2 expression (Gatto, D., at al. (2009) Guidance of B Cells by the Orphan G Protein-Coupled Receptor EBI2 Shapes Humoral Immune Responses. Immunity 31[2], 259-269; Pereira, J. P., et al. (2009) EBI2 mediates B cell segregation between the outer and centre follicle. Nature, 460). Once affinity maturation has been completed and the B cells are transformed into plasma B cells or memory B cells EBI2 expression is again highly expressed (FIGS. 20A and B). This pattern is the same for human and mouse B cells subsets (Longo, N. S., et al. (2009). Analysis of somatic hypermutation in X-linked hyper-IgM syndrome shows specific deficiencies in mutational targeting. Blood 113, 3706-3715; Luckey, C. J., et al. (2006). Memory T and memory B cells share a transcriptional program of self-renewal with long-term hematopoietic stem cells. Proc. Natl. Acad. Sci. USA 103, 3304-3309).

EBI2 has been originally identified by its up-regulation in B cells infected with Epstein-Barr virus (Birkenbach 1993). Conducting a FACS (fluorescence-activated cell sorting) experiment using an anti-EBI2 monoclonal antibody (Eurocreen) we find that this EBV-infected human B cell line expresses high levels of EBI2 on the cell surface.

Methodology for Generation of EBV-Transformed Peripheral B Lymphocytes.

Human peripheral B lymphocytes (PBL) were prepared from peripheral blood as a cell suspension by centrifugation on Ficoll plaque. PBL were rinsed in PBS and resuspended in complete RPMI 1640 medium (10% FCS and antibiotics) at the concentration of $2 \times 10^7$/cell/ml. Cells were divided in aliquots of 500 µl and seeded in 24 well plates. To each well ($10^7$ PBL), 500 µl of the B95-8 cell line supernatants (containing Epstein Barr virus) were added. The B95-8 cell line is a cell line used to produce EBV (American Type Culture Collection, Cat. CRL-1612). 0.8 μg/ml cyclosporin A (CsA) is added to each well. The cells are fed once a week by exchanging about half of the medium with fresh one containing 0.8 μg/ml CsA. This treatment is repeated for over 3 weeks until clusters of growing cells are visible. Single clusters are transferred to small culture flasks and the transformed cells are further expanded. Most transformed cells are from a B cell lineage. Aliquots of cells are frozen as soon as the cells are growing well. Frozen aliquots (1 ml, around $10^7$ cells) are thawed and diluted in RPMI 1640, 10% FCS, 50 μg/ml gentamicin and passaged by diluting ¼ to ⅛.

We find that 7a,25DHC can potently attract these EBV-infected B cells in a trans well assay system. As a control, the concentration of 7a,25DHC was identical in both compartments (FIG. 23).

In a second set of experiments we tested a Burkitt's lymphoma pre B cell line called RS11846 (provided by Dr. John C. Reed, Burnham Institute for Medical Research, La Jolla, USA; Gauwerky, C. E., et al. (1988). Pre-B-cell leukemia with at (8; 14) and at (14; 18) translocation is preceded by follicular lymphoma. Oncogene 2, 431-435.; Reed, J. C. et al. (1993). Somatic point mutations in the translocated bcl-2 genes of non-Hodgkin's lymphomas and lymphocytic leukemias: implications for mechanisms of tumor progression. Leuk. Lymphoma 10, 157-163.). Inspection of DNA array data (BioGPS) indicated that this cell line has high expression levels of endogenous EBI2.

We find that 7a,25DHC can potently attract RS11846 cells and that this attraction can be blocked by pertussis toxin, a reagent which blocks signalling of Gαi-coupled receptors by ADP-ribosylation of the Gαi subunit. Similarly to classical chemokines, we find a bell-shaped activity curve which indicates reduced attraction at high compound concentrations (FIGS. 24 A and B).

We also conducted cell migration experiments of RS11846 cells with a set of different oxysterols. The results (FIG. 25) show a clear correlation between the potency of different oxysterols in attracting RS11846 cells and the potency of these compounds in cell-based assays for functional activation of EBI2 (FLIPR, GTPgS) or EBI2 radioligand binding assays (see Table 3).

Oxysterol-mediated chemoattraction is not limited to B-cells but can also be observed with other immune cells expressing EBI2. Messenger RNA expression analysis of different human immune cells indicated that myeloid and plasmacytoid dendritic cells are highly expressing EBI2 (FIG. 26).

In order to generate sufficient numbers of dendritic cells (DC) we isolated bone marrow from wild type and EBI2-deficient mice (Deltagen) and treated them in culture for 7-8 days with murine IL4 and murine GM-CSF. Using this protocol a homogenous population of dendritic cells can be generated. We find that while DCs from wild type animals migrate towards 7a,25DHC, DCs from EBI2(−/−) mice do not migrate towards 7a,25DHC. This result demonstrates that chemoattractant properties of 7a,25DHC are mediated by EBI2 (FIG. 27).

Immune Challenge of EBI2 Knockout Mice (−/−)

Identification of the chemoattractant properties of oxysterols on immune cells suggested that ablation of EBI2 will have an impact on the proper trafficking of EBI2 expressing cells under various physiological conditions. Thus, we challenged wild-type and EBI2(−/−) mice with nitro-phenyl chicken gamma globulin (NP-CGG) and alum.

Immunisation of EBI2(−/−), and Wild Type Mice with Nitrophenyl-Chicken Gamma Globulin (NP-CGG)

Methodology

After pre-bleeding NP-CGG, immunization of EBI-2 ko mice or littermates was performed by injecting i.p. 200 μl of 50 μg NP(15)-CGG (Biosearch Technologies, Inc.; # N-5055) in Alum (Serva; #12261). Seven days thereafter serum was taken and NP-specific IgG1 and IgM analysed in ELISA.

ELISA Measurement of Nitorphenhyl-Specific Immunoglobulins

IgG1 and IgM anti-NP ELISA was performed by coating 96-well plates (Costar; #9018) with 10 μg ml$^{-1}$ NP(23)BSA (Biosearch Technologies, Inc.; #N-5050) in PBS (Gibco; #14040-091) over night at RT, and blocked with PBS/1% BSA/0.05% Tween 20 for 1 h at RT. Serum samples were serially diluted (1:3) starting at 1:50 in PBS/1% BSA/0.05% Tween 20 (=reagent buffer) in duplicates and incubated for 2 h at *25° C., and NP-binding IgG1 and IgM was detected using biotin-conjugated rat anti-mouse IgG1 (Zymed; #04-6140) or biotin-conjugated goat anti-mouse IgM (Southern Biotech; #1020-08), followed by Europium-conjugated streptavidin (Wallac; #1244-360). After each incubation step plates were washed 6 times with PBS/0.05% Tween 20). For measuring Europium-related light emission Enhancement Solution™ (Wallac; #1244-105) was added and plates measured in a Victor 2 Device™ (Wallac; 1420 Multilabel Counter) using the default Europium program. The NP-specific IgG1 and IgM titers were calculated by determining the titers at 50% max., groups averaged, and displayed as mean of titers 50% max. +/−STD, and Median. Seven days after immune challenge we measured immunoglobulin levels. While there are no alteration in the IgM expression level (FIG. 28A), we find a blunted IgG1 response in that the EBI2(−/−) mice only produce about half of the titer compared to wild type animals (FIG. 28B).

5.20 Results

Our findings provide an unanticipated link between recent results which have identified a crucial role for EBI2 in promoting B-cell localization within lymphoid organs (Pereira, J. P., et al. (2009) EBI2 mediates B-cell segregation between the outer and centre follicle. Nature 460[7259], 1122-1; Gatto, D., et al (2009) Guidance of B Cells by the Orphan G Protein-Coupled Receptor EBI2 Shapes Humoral Immune Responses. Immunity 31 [2], 259-269) and experiments identifying mechanisms by which oxysterols shape the adaptive immune response (Bauman, D. R., et al., (2009). 25-Hydroxycholesterol secreted by macrophages in response to Toll-like receptor activation suppresses immunoglobulin A production. Proc. Natl. Acad. Sci. U.S.A 106, 16764-16769; Diczfalusy, U., et al. (2009). Marked up-regulation of cholesterol 25-hydroxylase expression by lipopolysaccharide. J. Lipid Res, in press) and establish a new physiological dimension for these bioactive signalling molecules.

The invention claimed is:

1. A method of identifying a modulator that inhibits the binding between 7,25-dihydroxycholesterol (7,25DHC), 7,27-dihydroxycholesterol (7,27DHC), 7-hydroxycholesterol (7HC) or 25-hydroxycholesterol (25HC) and Epstein-Barr Virus induced receptor 2 (EBi2), wherein said method comprises;
 (a) providing a candidate modulator;
 (b) incubating said modulator with 7,25DHC, 7,27DHC, 7HC or 25HC and EBi2;
 (c) determining whether the binding between 7,25DHC, 7,27DHC, 7HC or 25HC and EBi2 is inhibited in the presence of said candidate modulator compared to the binding between 7,25DHC, 7,27DHC, 7HC or 25HC and EBi2 in the absence of said candidate modulator.

2. The method of claim 1 wherein 7,25DHC is 7a,25DHC or 7b,25DHC.

3. The method of claim 1 wherein 7,27DHC is 7a,27DHC or 7b,27DHC.

4. The method of claim 1 wherein 7HC is 7aHC or 7bHC.

5. The method of claim 1 wherein said method comprises identifying a modulator of the binding between 7,25DHC and EBi2.

6. The method of claim 1 wherein said method comprises identifying a modulator of the binding between 7,27DHC and EBi2.

7. The method of claim 1 wherein said method comprises identifying a modulator of the binding between 7HC and EBi2.

8. The method of claim 1 wherein said method comprises identifying a modulator of the binding between 25HC and EBi2.

* * * * *

SEQUENCE LISTING

```
<160> NUMBER OF SEQ ID NOS: 4

<210> SEQ ID NO 1
<211> LENGTH: 19
<212> TYPE: RNA
<213> ORGANISM: Homo sapiens

<400> SEQUENCE: 1
gaagcuucgu uucucuaau                                                        19

<210> SEQ ID NO 2
<211> LENGTH: 19
<212> TYPE: RNA
<213> ORGANISM: Homo sapiens

<400> SEQUENCE: 2
gcaggaggcu gaaaggauu                                                        19

<210> SEQ ID NO 3
<211> LENGTH: 19
<212> TYPE: RNA
<213> ORGANISM: Homo sapiens

<400> SEQUENCE: 3
gucaguguau cgauuucua                                                        19

<210> SEQ ID NO 4
<211> LENGTH: 19
<212> TYPE: RNA
<213> ORGANISM: Homo sapiens

<400> SEQUENCE: 4
caugcuaucu gccagaaau                                                        19
```